(12) United States Patent
Hans et al.

(10) Patent No.: US 9,629,891 B2
(45) Date of Patent: Apr. 25, 2017

(54) PRODUCTS AND METHODS FOR AORTIC ABDOMINAL ANEURYSM

(71) Applicant: NATIONWIDE CHILDREN'S HOSPITAL, INC., Columbus, OH (US)

(72) Inventors: Chetan Hans, Upper Arlington, OH (US); Vidu Garg, Columbus, OH (US)

(73) Assignee: NATIONWIDE CHILDREN'S HOSPITAL, INC., Columbus, OH (US)

( * ) Notice: Subject to any disclaimer, the term of this patent is extended or adjusted under 35 U.S.C. 154(b) by 0 days.

(21) Appl. No.: 14/352,169

(22) PCT Filed: Oct. 17, 2012

(86) PCT No.: PCT/US2012/060592
§ 371 (c)(1),
(2) Date: Apr. 16, 2014

(87) PCT Pub. No.: WO2013/059302
PCT Pub. Date: Apr. 25, 2013

(65) Prior Publication Data
US 2014/0256655 A1    Sep. 11, 2014

Related U.S. Application Data

(60) Provisional application No. 61/547,903, filed on Oct. 17, 2011.

(51) Int. Cl.
| A61K 38/00 | (2006.01) |
| A61K 38/05 | (2006.01) |
| A61K 31/192 | (2006.01) |
| A61K 31/223 | (2006.01) |

(52) U.S. Cl.
CPC ............ *A61K 38/05* (2013.01); *A61K 31/192* (2013.01); *A61K 31/223* (2013.01)

(58) Field of Classification Search
CPC ......... A61K 45/06; A61K 31/00; A61K 38/18
See application file for complete search history.

(56) References Cited

U.S. PATENT DOCUMENTS

| 5,703,129 | A | 12/1997 | Felsenstein et al. |
| 6,448,229 | B2 | 9/2002 | Teall |
| 6,683,091 | B2 | 1/2004 | Asberom et al. |
| 6,756,511 | B2 | 6/2004 | Castro Pineiro et al. |
| 6,890,956 | B2 | 5/2005 | Churcher et al. |
| 6,984,626 | B2 | 1/2006 | Nadin et al. |
| 6,995,155 | B2 | 2/2006 | Churcher et al. |
| 2005/0075320 | A1 | 4/2005 | Nadin et al. |
| 2005/0143369 | A1 | 6/2005 | Castro Pineiro et al. |
| 2005/0261276 | A1 | 11/2005 | Crawforth et al. |
| 2006/0004004 | A1 | 1/2006 | Asberom et al. |
| 2006/0009467 | A1 | 1/2006 | Josien et al. |
| 2006/0030694 | A1 | 2/2006 | Kitajewski et al. |
| 2007/0026042 | A1* | 2/2007 | Narayanan ............... 424/426 |
| 2011/0082114 | A1 | 4/2011 | Wood |

FOREIGN PATENT DOCUMENTS

| WO | WO-01/70677 A1 | 9/2001 |
| WO | WO-02/081435 A1 | 10/2002 |
| WO | WO-03/018543 A1 | 3/2003 |

OTHER PUBLICATIONS

Deangelo, A phase I clinical trial of the notch inhibitor MK-0752 in patients with T-cell acute lymphoblastic leukemia/lymphoma (T-ALL) and other leukemias, Journal of Clinical Oncology, 2006 ASCO Annual Meeting Proceedings, Post-Meeting Edition, vol. 24, No. 18S, 2006: 6585.*
Piggott, Blocking the NOTCH Pathway Inhibits Vascular Inflammation in Large Vessel Vasculitis, Circulation, Jan. 25, 2011; 123(3):309-318.*
Zheng et. al., Notch γ-Secretase Inhibitor Dibenzazepine Attenuates Angiotensin II-Induced Abdominal Aortic Aneurysm in ApoE Knockout Mice by Multiple Mechanisms, PLOS ONE, Dec. 2013, vol. 8, Issue 12.*
Funahashi et. al. Notch modulates VEGF action in endothelial cells by inducing Matrix Metalloprotease activity, Vascular Cell 2011, 3:2 (See ISR).*
Baxter et al., Medical management of small abdominal aortic aneurysms, Circulation, 117(14):1883-9 (2008).
Bray et al., Notch signalling: a simple pathway becomes complex, Nat. Rev. Mol. Cell Biol., 7(9):678-89 (2006).
Bruemmer et al., Relevance of angiotensin II-induced aortic pathologies in mice to human aortic aneurysms, Ann. NY Acad. Sci., 1245:7-10 (2011).
Cho et al., Decreased collagen and increased matrix metalloproteinase-13 in experimental abdominal aortic aneurysms in males compared with females, Surgery, 147(2):258-67 (2010).
Cooper et al., Role of medical intervention in slowing the growth of small abdominal aortic aneurysms, Postgrad. Med. J., 85(1010):688-92 (2009).
Daugherty et al., Angiotensin II promotes atherosclerotic lesions and aneurysms in apolipoprotein E-deficient mice, J. Clin. Invest., 105(11):1605-12 (2000).
Daugherty et al., Mechanisms of abdominal aortic aneurysm formation, Curr. Artheroscler. Rep., 4(3):222-7 (2002).
Daugherty et al., Mouse models of abdominal aortic aneurysms, Arterioscler. Thromb. Vasc. Biol., 24(3):429-34 (2004).
Evin et al., A synthetic substrate assay for the gamma-secretase of the beta-A4 amyloid of Alzheimer's disease, J. Pept. Sci., 1(2):132-9 (1995).
Funahashi et al., Notch modulates VEGF action in endothelial cells by inducing Matrix Metalloprotease activity, Vasc. Cell, 3(1):2 (2011).
Garg et al., Mutations in NOTCH1 cause aortic valve disease, Nature, 437(7056):270-4 (2005).
Golledge et al., Circulating markers of abdominal aortic aneurysm presence and progression, Circulation, 118(23):2382-92 (2008).

(Continued)

*Primary Examiner* — Jeanette Lieb
(74) *Attorney, Agent, or Firm* — Marshall, Gerstein & Borun LLP

(57) ABSTRACT

This invention relates to the treatment of aortic abdominal aneurysm. In particular, the invention relates to products and methods that inhibit Notch signaling to treat a patient developing or suffering from an aortic abdominal aneurysm.

6 Claims, 11 Drawing Sheets

(56) References Cited

OTHER PUBLICATIONS

Gridley, Notch signaling in vascular development and physiology, Development, 134(15):2709-18 (2007).

Guo et al., Role of angiotensin II type 1 receptor in angiotensin II-induced cytokine production in macrophages, J. Interferon Cytokine Res., 31(4):351-61 (2011).

Hans et al., Opposing roles of PARP-1 in MMP-9 and TIMP-2 expression and mast cell degranulation in dyslipidemic dilated cardiomyopathy, Cardiovasc. Pathol., 20:e57-e68 (2011).

Hans et al., Differential effects of PARP inhibition on vascular cell survival and ACAT-1 expression favouring ahterosclerotic plaque stability, Cardiovasc. Res., 78:429-39 (2008).

Hoke et al., In vitro gamma-secretase cleavage of the Alzheimer's amyloid precursor protein correlates to a subset of presenilin complexes and is inhibited by zinc, FEBS J., 272(21):5544-57 (2005).

Hui-Yuen et al., TNF-alpha is necessary for induction of coronary artery inflammation and aneurysm formation in an animal model of Kawasaki disease, J. Immunol., 176(10):6294-301 (2006).

Hurks et al., Different effects of commonly prescribed statins on abdominal aortic aneurysm wall biology, Eur. J. Vasc. Endovasc. Surg., 39(5):569-76 (2010).

International Preliminary Report on Patentability, corresponding International Application No. PCT/US12/60592, Apr. 22, 2014.

International Search Report and Written Opinion, corresponding International Application No. PCT/US12/60592, mailing date Jan. 18, 2013.

Jones et al., Interleukin-6 (IL-6) and the prognosis of abdominal aortic aneurysms, Circulation, 103(18):2260-5 (2001).

Keeling et al., An overview of matrix metalloproteinases in the pathogenesis and treatment of abdominal aortic aneurysms, Vasc. Endovascular Surg., 39(6):457-64 (2005).

Kopan et al., The canonical Notch signaling pathway: unfolding the activation mechanism, Cell, 137(2):216-33 (2009).

Lanz et al., The gamma-secretase inhibitor N-[N-(3,5-difluorophenacetyl)-L-alanyl]-S-phenylglycine t-butyl ester reduces A beta levels in vivo in plasma and cerebrospinal fluid in young (plaque-free) and aged (plaque-bearing) Tg2576 mice, J. Pharmacol. Exp. Ther., 305(3):864-71 (2003).

Loane et al., Amyloid precursor protein secretases as therapeutic targets for traumatic brain injury, Nat. Med., 15(4):377-9 (2009).

McKellar et al., Novel NOTCH1 mutations in patients with bicuspid aortic valve disease and thoracic aortic aneurysms, J. Thorac. Cardiovasc. Surg., 134(2):290-6 (2007).

Monsalve et al., Notch-1 up-regulation and signaling following macrophage activation modulates gene expression patterns known to affect antigen-presenting capacity and cytotoxic activity, J. Immunol., 176(9):5362-73 (2006).

Moxon et al., Diagnosis and monitoring of abdominal aortic aneurysm: current status and future prospects, Curr. Probl. Cardiol., 35(10):512-48 (2010).

Nigam et al., Notch1 represses osteogenic pathways in aortic valve cells, J. Mol. Cell Cardiol., 47(6):828-34 (2009).

Nus et al., Diet-induced aortic valve disease in mice haploinsufficient for the Notch pathway effector RBPJK/CSL, Arterioscler. Thromb. Vasc. Biol., 31(7):1580-8 (2011).

Olson et al., Recent progress in the medicinal chemistry of gamma-secretase inhibitors, Curr. Top Med. Chem., 8(1):17-33 (2008).

Osipo et al., Off the beaten pathway: the complex cross talk between Notch and NF-kappaB, Lab. Invest., 88(1):11-7 (2008).

Oumouna-Benachour et al., Poly(ADP-ribose) polymerase inhibition reduces atherosclerotic plaque size and promotes factors of plaque stability in apolipoprotein E-deficient mice: effects on macrophage recruitment, nuclear factor-kappaB nuclear translocation, and foam cell death, Circulation, 115(18):2442-50 (2007).

Parry et al., Markers of inflammation in men with small abdominal aortic aneurysm, J. Vasc. Surg., 52(1):145-51 (2010).

Piggott et al., Blocking the NOTCH pathway inhibits vascular inflammation in large-vessel vasculitis, Circulation, 123(3):309-18 (2011).

Pinnix et al., A novel gamma-secretase assay based on detection of the putative C-terminal fragment-gamma of amyloid beta protein precursor, J. Biol. Chem., 276(1):481-7 (2001).

Rush et al., Whole genome expression analysis within the angiotensin II-apolipoprotein E deficient mouse model of abdominal aortic aneurysm, BMC Genomics, 10:298 (2009).

Sernee et al., Selecting cells with different Alzheimer's disease gamma-secretase activity using FACS. Differential effect on presenilin exon 9 gamma- and epsilon-cleavage, Eur. J. Biochem., 270(3):495-506 (2003).

Shimizu et al., Mouse jagged1 physically interacts with notch2 and other notch receptors. Assessment by quantitative methods, J. Biol. Chem., 274(46):32961-9 (1999).

Shimizu et al., Physical interaction of Delta1, Jagged1, and Jagged2 with Notch1 and Notch3 receptors, Biochem. Biophys. Res. Commun., 276(1):385-9 (2000).

Sjolund et al., Suppression of renal cell carcinoma growth by inhibition of Notch signaling in vitro and in vivo, J. Clin. Invest., 118(1):217-28 (2008).

Talora et al., Notch signaling and diseases: an evolutionary journey from a simple beginning to complex outcomes, Biochim. Biophys. Acta, 1782(9):489-97 (2008).

Tieu et al., An adventitial IL-6/MCP1 amplification loop accelerates macrophage-mediated vascular inflammation leading to aortic dissection in mice, J. Clin. Invest., 119(12):3637-51 (2009).

Trollope et al., Animal models of abdominal aortic aneurysm and their role in furthering management of human disease, Cardiovasc. Pathol., 20(2):114-23 (2011).

Wang et al., Down-regulation of Notch-1 and Jagged-1 inhibits prostate cancer cell growth, migration and invasion, and induces apoptosis via inactivation of Akt, mTOR, and NF-kappaB signaling pathways, J. Cell Biochem., 109(4):726-36 (2010).

Wang et al., Mu opiate receptor: cDNA cloning and expression, Proc. Natl. Acad. Sci. USA, 90(21):10230-4 (1993).

Wanhainen, How to define an abdominal aortic aneurysm—influence on epidemiology and clinical practice, Scand. J. Surg., 97(2):105-9 (2008).

Xu et al., Gamma-Secretase: characterization and implication for Alzheimer disease therapy, Neurobiol. Agin, 23(6):1023-30 (2002).

\* cited by examiner

| | Notch1$^{+/-}$ | ApoE$^{-/-}$ | Notch1$^{+/-}$ApoE$^{-/-}$ |
|---|---|---|---|
| Saline | 0/3 | 0/5 | 0/5 |
| Angiotensin II | 0/6 | 8/10 | 2/10* |

*p<0.05

*Significant decrease in aortic width in ApoE$^{-/-}$ mice treated with DAPT at day-7 (pre-AngII), +3 and +8 (post-AngII) days of AngII*

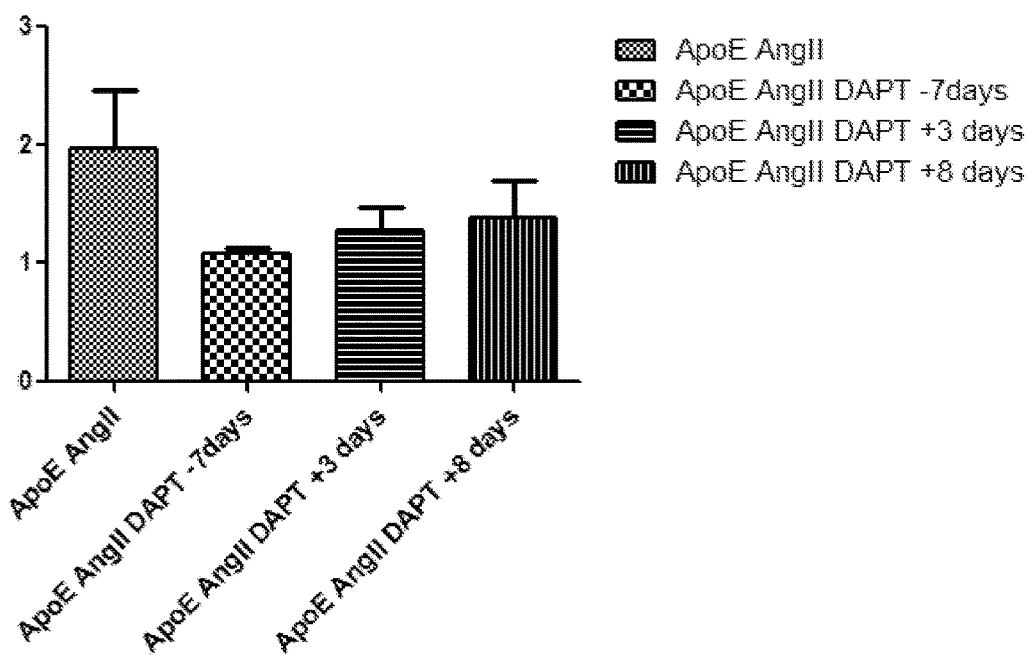

| Bonferroni's Multiple Comparison Test | Mean Diff. | t | Significant? P < 0.05? | Summary | 95% CI of diff |
|---|---|---|---|---|---|
| ApoE AngII vs ApoE AngII DAPT -7days | 0.8981 | 4.807 Yes | *** | | 0.3609 to 1.435 |
| ApoE AngII vs ApoE AngII DAPT +3 days | 0.7025 | 4.263 Yes | ** | | 0.2287 to 1.176 |
| ApoE AngII vs ApoE AngII DAPT +8 days | 0.5878 | 3.567 Yes | ** | | 0.1140 to 1.062 |
| ApoE AngII DAPT -7days vs ApoE AngII DAPT +3 days | -0.1957 | 1.187 No | ns | | -0.6694 to 0.2781 |
| ApoE AngII DAPT -7days vs ApoE AngII DAPT +8 days | -0.3103 | 1.883 No | ns | | -0.7841 to 0.1634 |
| ApoE AngII DAPT +3 days vs ApoE AngII DAPT +8 days | -0.1147 | 0.8234 No | ns | | -0.5151 to 0.2857 |

Figure 7

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
ctggatcgga accaaatgag                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
aaggcatcac agtccgagtc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ctaccccaat ttccaatgct                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
accacagtga ggaatgtcca                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cccactctga cccctttact                                              20

<210> SEQ ID NO 6
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 6
tttgagtcct tgatggtcgt                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
cccacgtgtt gagatcattg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
cactgggtaa aggggagtga                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ggctgctgta acgatgaagc                                              20

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
ttaactcaag ctgcctcgc                                               19

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
ctcggaggtt cacctcactg t                                            21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
tcctgatcca agtgctgcag a                                            21

```
<210> SEQ ID NO 13
<211> LENGTH: 19
<212> TYPE: DNA
<213> ORGANISM: Artificial Sequence
<220> FEATURE:
<223> OTHER INFORMATION: Synthetic primer

<400> SEQUENCE: 13
gtgatccctg ggcctggtg                                               19

<210> SEQ ID NO 14
<211> LENGTH: 22
<212> TYPE: DNA
<213> ORGANISM: Artificial Sequence
<220> FEATURE:
<223> OTHER INFORMATION: Synthetic primer

<400> SEQUENCE: 14
ggaaacgaat acacggtgat gg                                           22

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
taccagctcc caaaatcctg                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
tctgctaatt ccagcctcgt                                              20
```

PRODUCTS AND METHODS FOR AORTIC ABDOMINAL ANEURYSM

This application claims the benefit of the filing date of U.S. Provisional Patent Application No. 61/547,903 filed Oct. 17, 2011, which is incorporated by reference herein in its entirety.

FIELD OF THE INVENTION

This invention relates to the treatment of an aortic abdominal aneurysm. In particular, the invention relates to products and methods that inhibit Notch signaling to treat patients developing or suffering from an aortic abdominal aneurysm.

INCORPORATION BY REFERENCE OF THE SEQUENCE LISTING

This application contains, as a separate part of disclosure, a Sequence Listing in computer-readable form (filename: 46359PCT_SeqListing.txt; 3,330 bytes—ASCII text file) which is incorporated by reference herein in its entirety.

BACKGROUND

Abdominal aortic aneurysm (AAA) is among the fifteen leading causes of death in the United States and has a prevalence of ~10% in individuals over 60 years of age [Moxon et al., Current Problems in Cardiology, 35:512-548 (2010)]. AAA is characterized by extensive and permanent remodeling of the aortic wall, which results in a weakened and dilated aorta that is prone to rupture [Daugherty et al., Curr. Atheroscler. Rep., 4:222-227 (2002); Wanhainen, Scand. J. Surg., 97:105-109 (2008)]. Chronic inflammation caused by excessive macrophage infiltration of the aortic wall plays a key role in the pathophysiology of the disease by causing degradation of the extracellular matrix (ECM) along with apoptosis of endothelial cells (ECs) and vascular smooth muscle cells (VSMCs) [Daugherty et al., Curr. Atheroscler. Rep., 4:222-227 (2002); Daugherty et al., Arterioscler. Thromb. Vasc. Biol., 24:429-434 (2004)]. Several pharmacologic therapies including statins, β-blockers and antibiotics have all failed in large clinical trials to prevent AAA, and there are no currently approved non-surgical therapies to treat AAA [Baxter et al. Circulation, 117:1883-1889 (2008); Hurks et al., European Journal of Vascular and Endovascular Surgery, 39:569-576 (2010)].

The pathophysiology of AAA has been well-described by analysis of both diseased human aortas and animal models. Initially, there is infiltration of inflammatory cells into the aortic wall followed by destruction of the normal aortic wall architecture. Human and mouse histologic studies of AAA have demonstrated the presence of extensive inflammatory macrophages and lymphocytes as major cellular components of the diseased aneurysmal tissue [Parry et al., Journal of Vascular Surgery, 52:145-151 (2010)]. These infiltrating cells exacerbate tissue injury by releasing cytokines (IL-6, interleukin-6; TNF-α, tumor necrosis factor-α), chemokines (MCP-1, monocyte chemotactic protein-1; CXCL-10, C—X—C motif chemokine-10) and adhesion molecules (ICAM-1, intercellular adhesion molecule-1; VCAM-1, vascular cell adhesion molecule-1) [Hui-Yuen et al., J. Immunol., 176:6294-6301 (2006); Jones et al., Circulation, 103: 2260-2265 (2001); Rush et al., BMC Genomics, 10:298 (2009); Tieu et al., J. Clin. Invest., 119: 3637-3651 (2009)]. Excessive infiltration of macrophages and apoptosis of ECs and VSMCs are the most potent stimulators for the formation and progression of AAA because of their contribution to the widespread matrix degradation. Increased activation of matrix metalloproteinases (MMPs) results in both the degradation of collagen and collagenous matrix by MMP3 and MMP13 and the dissolution of the elastin by MMP2 and MMP9 [Cho et al., Surgery, 147:258-267 (2010); Keeling et al., Vascular and Endovascular Surgery, 39:457-464 (2005)]. This enhanced degradation of structural proteins, together with a reduced capacity to synthesize new matrix proteins, likely acts in synergy to progressively weaken the aortic wall, predisposing it to rupture. Various animal models of AAA are known in the art [Trollope et al., Cardiovascular Pathology, 20:114-123 (2011)].

The Notch signaling pathway is important in a wide spectrum of developmental processes, including angiogenesis, cardiovascular development and smooth muscle differentiation, but recently it has been studied in the molecular pathogenesis of cancer, cardiovascular disease and a diverse array of inflammatory diseases [Garg et al., Nature, 437: 270-274 (2005); Gridley, Development, 134:2709-2718 (2007); Monsalve et al., J. Immunol., 176:5362-5373 (2006); Talora et al., Biochimica et Biophysica Acta (BBA)—Molecular Basis of Disease, 1782:489-497 (2008)]. The signaling pathway comprises of a family of four mammalian Notch receptors (1-4) that interact with the Jagged and Delta family of ligands [Kopan et al., Cell, 17:216-233 (2009)]. Notch1 is the best-studied receptor, and mutations in NOTCH1 have been linked to bicuspid aortic valve, aortic valve calcification, and thoracic aortic aneurysm (TAA) [Garg et al., Nature, 437:270-274 (2005); McKellar et al., J. Thorac. Cardiovasc. Surg., 134:290-296 (2007)]. In the canonical signaling pathway, Notch1 is activated after receptor-ligand binding at the cell surface, which induces proteolytic cleavage by several proteases, including γ-secretase. This results in the release and translocation of the Notch1 intracellular domain (NICD) into the nucleus where NICD binds and functions as a transcriptional activator [Bray, Nat. Rev. Mol. Cell. Biol., 7:678-689 (2006)]. Mice lacking Notch1 suffer embryonic lethality with profound cardiac and vascular defects, whereas heterozygous deletion of Notch1 is associated with aortic valve calcification [Gridley, Development, 134:2709-2718 (2007); Nigam et al., Journal of Molecular and Cellular Cardiology, 47:828-834 (2009); Nus et al., Arteriosclerosis, Thrombosis, and Vascular Biology, 31:1580-1588 (2011)]. In addition to its role in cardiovascular disease, Notch1 signaling has been shown to play a critical role in the development and activation of lymphocytes and macrophages via the upregulation of MCP-1 and ICAM-1 expression [Monsalve et al., J. Immunol., 76:5362-5373 (2006)]. Notch1 has also been suggested to regulate the expression of a variety of key inflammatory genes including MCP-1, inducible nitric oxide synthase (iNOS), ICAM-1, and VCAM-1 [Wang et al., J. Cell Biochem., 109:726-736 (2010)]. Several reports have shown decreased nuclear factor-κB (NF-κB) activity at basal levels and in response to external stimuli in mice with reduced Notch1 levels [Osipo et al., Lab. Invest., 88:11-17 (2008)]. However, the role of Notch signaling in the development and progression of AAA has not been previously studied.

There thus remains a need in the art for pharmacological treatments for AAA.

DESCRIPTION

In a first aspect, the invention provides a method of treating a patient developing (i.e., with aortic dilation, but less than a 50% increase in the aortic diameter from normal) or having an AAA (i.e., with an aortic diameter increased 50% or more from normal) by administering an inhibitor of a Notch signaling pathway. Inhibitors that inhibit the signaling of one or more of the Notch1, Notch2, Notch3 and Notch4 signaling pathways are contemplated. In some embodiments, the inhibitor is an inhibitor or a specific inhibitor of the Notch1 signaling pathway. In some embodiments, the inhibitor administered is an inhibitor or a specific inhibitor of the Notch2 signaling pathway. In some embodiments, the inhibitor administered is an inhibitor or a specific inhibitor of the Notch3 signaling pathway. In some embodiments, the inhibitor administered is an inhibitor or a specific inhibitor of the Notch4 signaling pathway. As an illustration using phrases relating to the Notch1 pathway, as used herein the phrase "an inhibitor of the Notch1 signaling pathway" means an inhibitor that inhibits the Notch1 signaling pathway but may also inhibit another Notch signaling pathway (e.g., the Notch2, Notch3 and/or Notch4 signaling pathway). As used herein the phrase "a specific inhibitor of the Notch1 signaling pathway" means an inhibitor that inhibits the Notch1 signaling pathway but does not detectably inhibit the Notch2, Notch3 or Notch4 signaling pathway in an in vitro assay. Thus, in some embodiments, the inhibitor administered is an inhibitor of one or more of the Notch signaling pathways. In some embodiments, more than one inhibitor is administered.

In some embodiments, the inhibitor slows or halts the progression of the AAA. In some embodiments, the inhibitor also stimulates regression of the AAA. The inhibitors are administered in therapeutically effective amounts to achieve the desired clinical result. As used herein, "progression" of an AAA is the increase in size of the AAA, while "regression" is a decrease in size of the AAA.

As used herein, an inhibitor of the Notch signaling pathway is a therapeutic capable of inhibiting Notch signaling. Examples of such inhibitors known in the art are the γ-secretase inhibitors N—[N-(3,5-Difluorophenacetyl)-L-alanyl]-S-phenylglycine t-butyl ester (also referred to as LY-374973 or DAPT) (Cayman Chemical or Enzo Life Sciences, Inc.) and cis-3-[3-[(3-chlorophenyl)sulfonyl]-4-(2,5-difluorophenyl)cyclohexyl]propanoicacid (also referred to as MK-0752). Examples of additional inhibitors are other γ-secretase inhibitors such as the γ-secretase inhibitor RO4929097 (Selleck Chemicals, Houston, Tex.) as well as the inhibitors described in U.S. Pat. Nos. 5,703,129; 6,448,229; 6,683,091; 6,756,511; 6,890,956; 6,984,626; and 6,995,155; WO 01/70677; WO 02/081435; WO 03/018543; WO 00/50391; U.S. Patent Application Publication No. 2006/0030694; U.S. Patent Application Publication No. 2006/0004004; U.S. Patent Application Publication No. 2006/0009467; U.S. Patent Application Publication No. 2005/0261276; U.S. Patent Application Publication No. 2005/0143369; and U.S. Patent Application Publication No. 2005/0075320. Yet other examples are [(2R,4R,5S)-2-Benzyl-5-(Boc-amino)-4-hydroxy-6-phenyl-hexanoyl]-Leu-Phe-NH$_2$ (BACHEM), L-685,458 (BioVision or Torcris Bioscience), γ-Secretase Inhibitor VI (EMD Millipore), γ-Secretase Inhibitor VII (EMD Millipore), γ-Secretase Inhibitor X (EMD Millipore), γ-Secretase Inhibitor XI (EMD Millipore), γ-Secretase Inhibitor XVII (EMD Millipore), γ-Secretase Inhibitor XXI (EMD Millipore), gamma-Secretase Inhibitor II (EMD Millipore), gamma-Secretase Inhibitor I (EMD Millipore), gamma-Secretase Inhibitor III (EMD Millipore), gamma-Secretase Inhibitor IV (EMD Millipore), gamma-Secretase Inhibitor IX (EMD Millipore), gamma-Secretase Inhibitor V (EMD Millipore), gamma-Secretase Inhibitor XII (EMD Millipore), gamma-Secretase Inhibitor XIII (EMD Millipore), gamma-Secretase Inhibitor XIV (EMD Millipore), gamma-Secretase Inhibitor XVI (EMD Millipore), gamma$_{40}$-Secretase Inhibitor XIX (EMD Millipore), Compound 34 (Enzo Life Sciences, Inc.), and Compound E (Enzo Life Sciences, Inc.).

NOTCH inhibitors that inhibit the NOTCH signaling pathway(s) by mechanisms other than by γ-secretase inhibition are also useful in methods of the invention. Inhibitors can inhibit aspects of NOTCH signaling including, but not limited to, assembly of the Notch complex; receptor cleavage and/or nuclear translocation; ligand turnover, cleavage and/or endocytosis; NOTCH trafficking to cell membrane; expression of ligands and/or receptors; NOTCH glycosylation; ubiquitination of NOTCH components including NOTCH intracellular domain; and expression and/or activity of co-factors or effectors (e.g., members of the MAML family, RBP-Jkappa/CBF-1). NOTCH inhibitors that inhibit matrix degradation, inhibit inflammation and/or direct M1/M2 polarization are also useful in methods of the invention.

Inhibitors contemplated by the invention other than small molecules include, but are not limited to, antibody-based polypeptides (e.g., a single chain antibody to Jagged), peptides such as extracellular domains, aptamers and microRNAs.

Assays known in the art identify other compounds that inhibit the NOTCH signaling pathway(s). These include, but are not limited to, enzymatic assays for inhibitors of γ-secretase or assays to identify agents that interfere with receptor binding. Enzymatic assays for identifying inhibitor of γ-secretase activity include, for example, assays using radiolabeled substrates followed by HPLC or TLC analysis [e.g., Evin, et al., *J. Pept. Sci.* 1(2):132-139 (1995)]; FACS assays [Sernee, et al., *Eur. J. Biochem.* 270:495-506 (2003)]; and other in vitro or in vivo assays [Pinnix, et al., *J. Biol. Chem.* 276:481-487 (2001); Xu, et al., *Neurobiol. Aging* 23(6): 1023-1030 (2002); and Holke, et al., *FEBS J.* 272:5544 (2005)]. Commercially available assays such as the QTL Lightspeed assay (QTL Biosystems, Santa Fe, N. Mex.) are also used.

Receptor binding assays that can be adapted to identify compounds that interfere with the binding of NOTCH ligands have been described in the art and are used in conjunction with the present invention. See, e.g., Shimizu, et al., *J. Biol. Chem.* 274(46):32961-32969 (1999); Shimizu, et al., *Biochem. Biophys. Res. Commun.* 276(1):385-389 (2000). In general, receptor binding assays are performed using a source of NOTCH receptor together with one of the ligands that are known to bind to the receptor and with the compound being tested for binding activity. As a source of receptor, mammalian cells that have been transformed to recombinantly express a NOTCH receptor may be used. The assay itself may be performed either with intact cells or with membranes prepared from the cells (see, e.g., Wang, et al., *Proc. Natl. Acad. Sci. USA* 90:10230-10234 (1993)). The membranes or cells are incubated with one of the ligands for the NOTCH receptor [e.g., Delta1 (Delta-like 1/Dll1), Delta3 (Delta-like 3/Dll3), Delta4 (Delta-like 4/Dll4), Jagged1 or Jagged 2] and with a preparation of the compound being tested. After binding is complete, the receptor is separated from the solution containing ligand and test compound, e.g., by filtration, and the amount of binding that has occurred is determined. Preferably, the ligand used is detectably labeled with a radioisotope such as $^{125}$I, however, fluorescent chemiluminescent or enzymatic labels can also be used.

An inhibitor of a Notch signaling pathway is formulated as a composition for administration according to techniques known in the art. A composition for administration includes at least an inhibitor and a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art [see, e.g., Reminpton's Pharmaceutical Sciences, 16.sup.th edition, E.W. Martin, Easton, Pa. (1980)]. In addition, compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants.

The invention is compatible with the delivery of inhibitors by any route known in the art, including peroral, internal, oral, rectal, nasal, lingual, transdermal, intravenous, intra-arterial, intramuscular, intraperitoneal, intracutaneous and subcutaneous routes. In cases where a compound is susceptible to degradation in the stomach of a patient, it may be enterically coated or it may be administered parenterally.

Compositions contemplated by the invention may contain any pharmaceutically acceptable form of an inhibitor (i.e., any form which maintains therapeutic activity and which does not cause unacceptable adverse effects when administered). For example, an inhibitor may be in the form of a pharmaceutically acceptable salt, ester or pro-drug.

Liquid dosage forms for oral administration include, but are not limited to, pharmaceutically acceptable emulsions, microemulsions, solutions, suspensions, syrups and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters. Solid dosage forms for oral administration include, but are not limited to, capsules, tablets, pills, powders or granules. In these dosage forms, the active compound will typically be mixed with at least one inert, pharmaceutically acceptable excipient or carrier such as sodium citrate, or diacalcium phosphate and/or: fillers or extenders such as starches, lactose, sucrose, glucose, mannitol and silicic acid; binders such as, for example, carboxymethyl cellulose, alginates, gelatin, polyvinylpyrrolidinone, and acacia, humectants such as glycerol; disintegrating agents such as calcium carbonate, silicates or sodium carbonate; solution retarding agents such as paraffin; absorption accelerators such as quaternary ammonium compound; wetting agents such as cetyl alcohol or glycerol monostearate; absorbents such as kaolin; and lubricants, such as talc, magnesium stearate; sodium lauryl sulphate, etc. In addition, dosage forms may include buffering and flavoring agents.

Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present.

On a biological level, sufficient inhibitor is administered to inhibit the NOTCH signaling pathway in the abdominal aorta where AAA develop. For example, a therapeutically effective amount of a γ-secretase inhibitor reduces γ-secretase activity by about 10%, 20%, 30%, 40%, 50%, 60%, 70%, 80%, 90% or more. The exact dosages given and amount of inhibitor are determined for individual inhibitors using methods that are well known in the art of pharmacology and may be further adjusted by physicians on a case-by-case basis based upon clinical considerations.

In some embodiments of methods of the invention, a patient receiving an inhibitor of a Notch signaling pathway also receives a statin, an anti-inflammatory or a lipid-lowering drug. In some embodiments of methods of the invention, a patient receiving an inhibitor of a Notch signaling pathway also receives a steroid such as dexamethasone.

BRIEF DESCRIPTION OF THE DRAWING

FIG. 3 shows quantitation of the TUNEL positive nuclei by Image Pro Plus indicating statistically significant decrease in apoptosis in the intimal (A) and medial/adventitial layer (B) of aorta in Notch1$^{+/-}$ and Notch1$^{+/-}$ApoE$^{-/-}$ mice as compared to ApoE$^{-/-}$ mice. Graph represents percentage of TUNEL positive cells per 100 cells identified by DAPI staining. Three separate regions are analyzed per genotype and means and standard deviation is shown. * p value<0.001;  p value<0.01; #, not significant.

FIG. 4 shows quantitation of decreased MCP-1 expression in the abdominal aorta of Notch1$^{+/-}$ApoE$^{-/-}$ mice in response to AngII as compared to ApoE$^{-/-}$ mice.

FIG. 7. Therapeutic pharmacological inhibition of Notch signaling attenuates aneurysm development in an AngII-induced mouse model of AAA. FIG. 7 shows the results of quantitative measurement of aortic width (mm) in the mice that were treated with Notch inhibitor started on Day 3 and Day 8 of AngII infusion as compared to untreated and prophylactic Notch inhibitor treatment.

EXAMPLES

Figure 1:
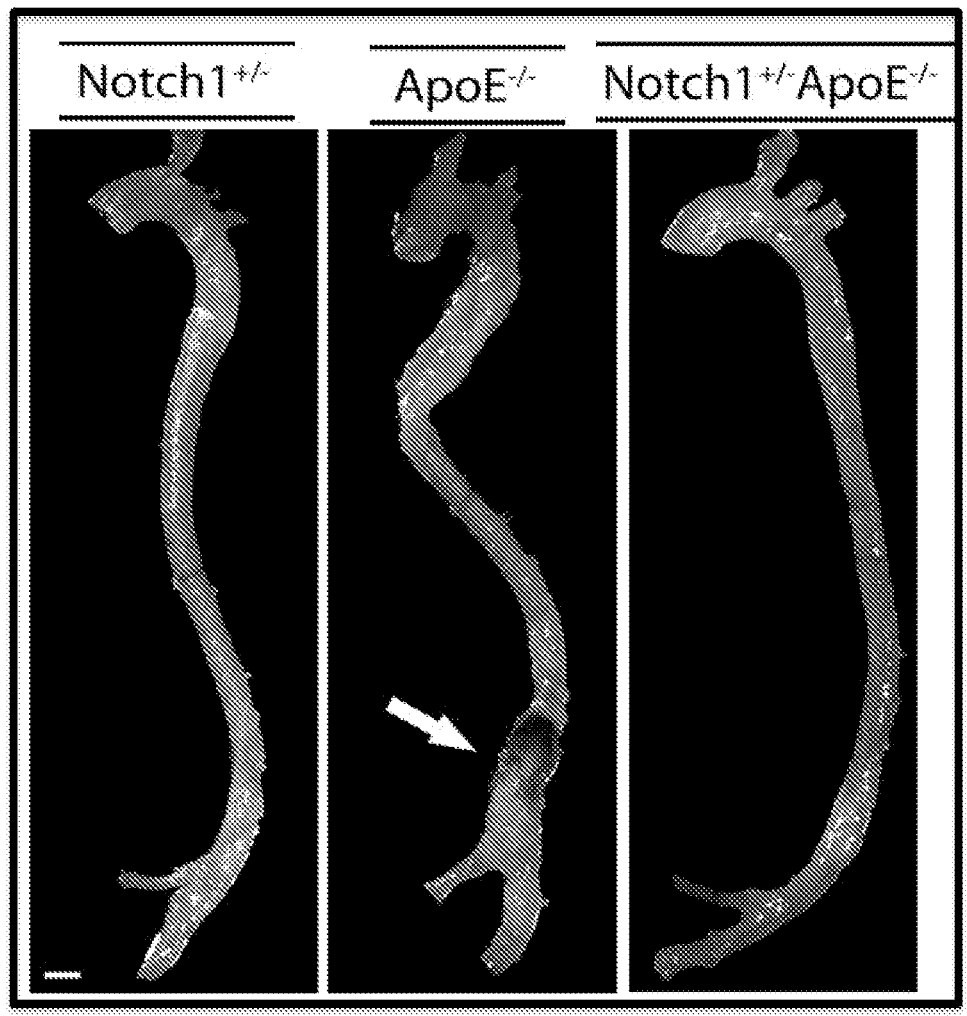
FIG. 1. Notch1 haploinsufficiency reduces the occurrence of AAA in ApoE$^{-/-}$ mice after 28 day AngII infusion. Representative aortas from transgenic mice treated AngII (A-C) are shown in FIG. 1. Aneurysm is observed in ApoE$^{-/-}$ mice treated with AngII (B) but is absent in Notch1$^{+/-}$ and Notch1$^{+/-}$ApoE$^{-/-}$ mice treated with AngII (A and C).

Thus, aspects and embodiments of the invention are illustrated by the following examples. Example 1 describes the activation of Notch1 in response to AngII in ApoE$^{-/-}$ mice. Example 2 shows Notch1 haploinsufficiency reduces the occurrence of AAA. Example 3 demonstrates Notch1 haploinsufficiency reduces macrophage infiltration at site of AAA. Example 4 shows inhibition of Notch1 downregulates expression of inflammatory mediators by macrophages. Example 5 shows Notch1 haploinsufficiency causes defects in macrophage migration and proliferation by differentially regulating M1/M2 polarization. Example 6 demonstrates prophylactic pharmacological inhibition of Notch signaling attenuates aneurysm development in an AngII-induced mouse model of AAA. Example 7 demonstrates therapeutic pharmacological inhibition of Notch signaling attenuates aneurysm development in an AngII-induced mouse model of AAA. Example 8 demonstrates pharmacological inhibition of Notch signaling prevents the progression of active AAA in an AngII-induced mouse model.

Example 1

Notch1 is Activated in Response to AngII in ApoE$^{-/-}$ Mice

To determine if Notch1 signaling is altered in the formation and progression of AAA, the expression of the Notch1 intracellular domain (NICD), the active form of Notch1, in the abdominal aorta was examined in the well-established AngII-induced mouse model of AAA. [Bruemmer et al., *Ann. N.Y. Acad. Sci.*, 1245:7-10 (2011)].

Six to eight week old ApoE$^{-/-}$ female mice in a C57BL/6J background and Notch1$^{+/-}$ male mice (Jackson Laboratory, Bar Harbor, Me.) were crossbred to generate Notch1$^{+/-}$ApoE$^{-/-}$ (F1) mice which were then interbred to obtain Notch1$^{+/-}$ApoE$^{-/-}$ (F2) mice. Finally, ApoE$^{-/-}$ mice were crossbred with Notch1$^{+/-}$ApoE$^{-/-}$ mice to obtain ApoE$^{-/-}$ and Notch1$^{+/-}$ApoE$^{-/-}$ littermates. Mice were kept on a 12 h/12 h light/dark cycle and allowed standard food chow and water ad libitum. Genotyping was performed using conditions specified by Jackson Laboratories. The mice were randomly assigned to receive either saline or angiotensin II (AngII). All animal experiments were approved by the Institutional Animal Care and Use Committee.

Mini osmotic pumps (Model 2004; Alzet, Cupertino, Calif.) containing AngII (1000 ng/min/kg) or saline were implanted subcutaneously in the neck region of anesthetized mice following standard protocol [Daugherty et al., *J. Clin. Invest.*, 105:1605-1612 (2000)]. Three independent experiments were performed to determine the effect of Notch1 haploinsufficiency on the formation of AAA. In one of these three experiments the effects of pharmacological inhibition of Notch were tested on AAA formation. Mice (n=3) were injected with a Notch inhibitor, DAPT (10 mg/kg dissolved in 10% ethanol, 90% corn oil), three times a week subcutaneously starting one week before the implantation of osmotic pump and continuing for an additional 28 days until the mice were sacrificed, as explained for FIG. 6. [Loane et al., *Nat. Med.*, 15:377-379 (2009); Lanz et al., *J. Pharmacol. Exp. Ther.*, 305:864-871 (2003); Sjolund et al., *J. Clin. Invest.*, 118:217-228 (2008)].

The abdominal region of the aorta were embedded in paraffin and serial sections (5 µM) were obtained. Sections were subjected to immunohistochemistry (IHC)/double immunofluorescence (IF) with antibodies to NICD (1:200; Abcam, Cambridge, Mass.), mouse monocyte-macrophage (1:100; MOMA-2 Abcam, Cambridge, Mass.), and MCP-1 (1:200; Abcam, Cambridge, Mass.), as described [Hans et al., *Cardiovasc. Pathol.*, 185:1894-902 (2011); Hans et al., *Cardiovasc. Res.*, 78:429-439 (2008); Oumouna-Benachour et al., *Circulation*, 115:2442-2450 (2007)]. Briefly, serial sections were deparaffinized, then antigen retrieval and blocking was performed. For NICD IHC, Vector ABC biotin kit and Vectastain DAB substrate (Vector Laboratories, Burlingame Calif.) were employed for the development of reaction and tissues were counterstained with hematoxylin to examine the nuclear localization of NICD. For double IF staining, Texas Red conjugated anti-rabbit IgG for MCP-1 and fluorescein conjugated rabbit anti-rat IgG for MOMA-2 (Vector lab) were used as secondary antibodies, and the nuclei were counter stained with 4',6-diamidino-2-phenylindole (DAPI). MCP-1 positive areas in the abdominal tissue were quantified with Image Pro plus software using the average values of positive immunostaining per area for five locations from 3 mice per group [Hans et al., *Cardiovasc. Pathol.*, 185:1894-902 (2011); Oumouna-Benachour et al., *Circulation*, 115:2442-2450 (2007)].

Transverse sections of the abdominal aorta from ApoE$^{-/-}$ mice demonstrated higher expression levels of NICD by immunohistochemistry in the aneurysmal region of mice treated with AngII as compared to saline. Expression of NICD protein was increased in both the medial and intimal layers of the aneurysmal abdominal aorta and was very prominent in the regions of active inflammation and elastin degradation. This observation suggested that activation of the Notch1 signaling pathway is associated with AAA.

Example 2

Notch1 Haploinsufficiency Reduces the Occurrence of AAA

To further investigate the role of Notch1 in the development of AAA, the effect of Notch1 haploinsufficiency on the incidence of AAA was studied in the AngII-induced mouse model. Notch1$^{+/-}$, ApoE$^{-/-}$ and Notch1$^{+/-}$ApoE$^{-/-}$ compound mutant mice were treated with AngII or saline for 28 days [Daugherty et al., *Curr. Atheroscler. Rep.*, 4:222-227 (2002); Daugherty et al., *Arterioscler. Thromb. Vasc. Biol.*, 24:429-434 (2004)].

Two dimensional (B-mode) in vivo ultrasound images were obtained at weekly intervals after the implantation of osmotic pumps using a VisualSonics Vevo2100 imaging system (Ontario, Canada) with a mechanical transducer (MS400). After 28 days, the animals were euthanized and the aortas were dissected and fixed in 10% formalin. Minimum and maximum diameters of each vessel were determined by digitalized measurement (Zeiss AxioImager upright microscope with brightfield).

Ultrasound imaging and direct examination of the abdominal aorta in experimental mice after 28 days demonstrated luminal expansion in ApoE$^{-/-}$ mice treated with AngII, while no luminal expansion was observed in the Notch1$^{+/-}$ApoE$^{-/-}$ mice. As expected, Notch1$^{+/-}$ and wild-type mice treated with AngII and Notch1$^{+/-}$, ApoE$^{-/-}$ and Notch1$^{+/-}$ApoE$^{-/-}$ mice treated with saline did not develop luminal expansion upon gross and ultrasonic examination.

After dissection of the aorta with removal of loose connective tissue, the aortas were examined for the presence of aortic dilation and aneurysm formation. ApoE$^{-/-}$ mice treated with AngII had a significantly increased maximal external diameter of the abdominal aorta versus saline treated ApoE$^{-/-}$ mice (P<0.001). Notch1$^{+/-}$ApoE$^{-/-}$ mice treated with AngII had statistically significant reduction in aortic width as compared to ApoE$^{-/-}$ mice treated with AngII (P<0.001). The aortic width of Notch1$^{+/-}$ApoE$^{-/-}$ mice in response to AngII was not statistically different from Notch1$^{+/-}$ mice treated with AngII or saline-treated controls. In total, 80% (8/10) of ApoE$^{-/-}$ mice treated with AngII developed AAA, as defined as a 50% increase in external aortic diameter, as compared to 20% (2/10) Notch1$^{+/-}$ApoE$^{-/-}$ mice treated with AngII (P<0.05; Table 1).

Histological examination of the abdominal aorta of the AngII and saline treated mutant mice was performed. The abdominal region of the aorta were embedded in paraffin and serial sections (5µM) were obtained. Sections were stained with hematoxylin and eosin (HE), elastin staining (Sigma, St. Louis, Mo.), and terminal deoxynucleotidyl transferase-mediated dUTP nick-end labeling (TUNEL) staining (Roche, Indianapolis, Ind.). Statistical comparisons were performed using either Student's t-test or one-way ANOVA followed by the Bonferroni's Multiple Comparison Test. GraphPad PRISM V5.0 (San Diego, Calif.) was used for these comparisons and a P value<0.05 was considered significant. For the statistical analysis of actual incidence, Fisher's exact test was employed using The SAS system.

Figure 3A:
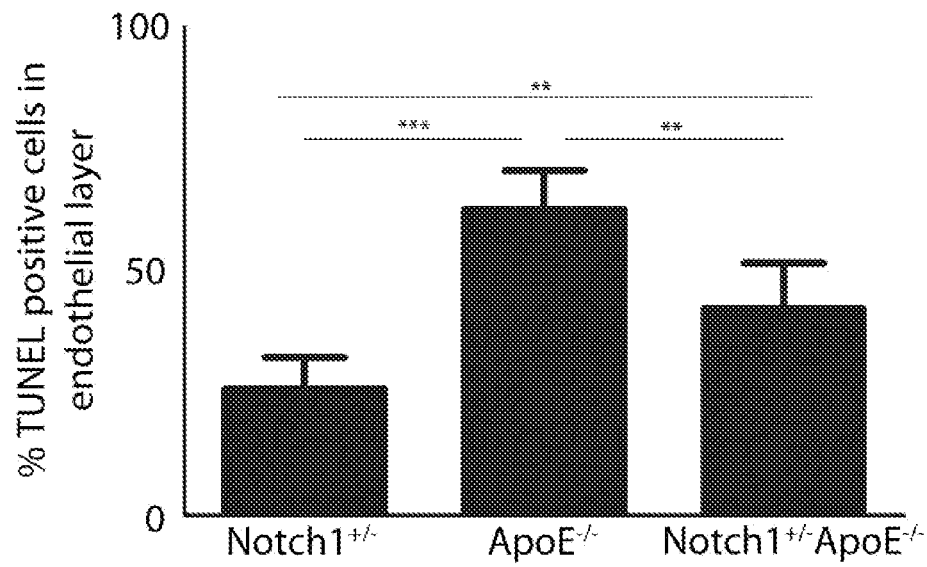
FIG. 3A-B. Notch1$^{+/-}$ApoE$^{-/-}$ mice treated with AngII do not exhibit histologic evidence of abdominal aneurysm, elastin degradation or apoptosis. Transverse sections of abdominal aorta were stained for hematoxylin and eosin. Adventitial remodeling with infiltration of inflammatory cells, elastin degradation and thrombus were observed in the aorta of ApoE$^{-/-}$ mice infused with AngII. No changes except mild intimal thickening was observed in Notch1$^{+/-}$ and Notch1$^{+/-}$ApoE$^{-/-}$ mice infused with AngII. Elastin staining demonstrated elastin fragmentation in ApoE$^{-/-}$ mice which was not seen in Notch1$^{+/-}$ and Notch1$^{+/-}$ApoE$^{-/-}$ mice. TUNEL staining shows decreased apoptosis in all layers of the aortic wall of Notch1$^{+/-}$ and Notch1$^{+/-}$ApoE$^{-/-}$ mice as compared to ApoE$^{-/-}$ mice.
Figure 3B:
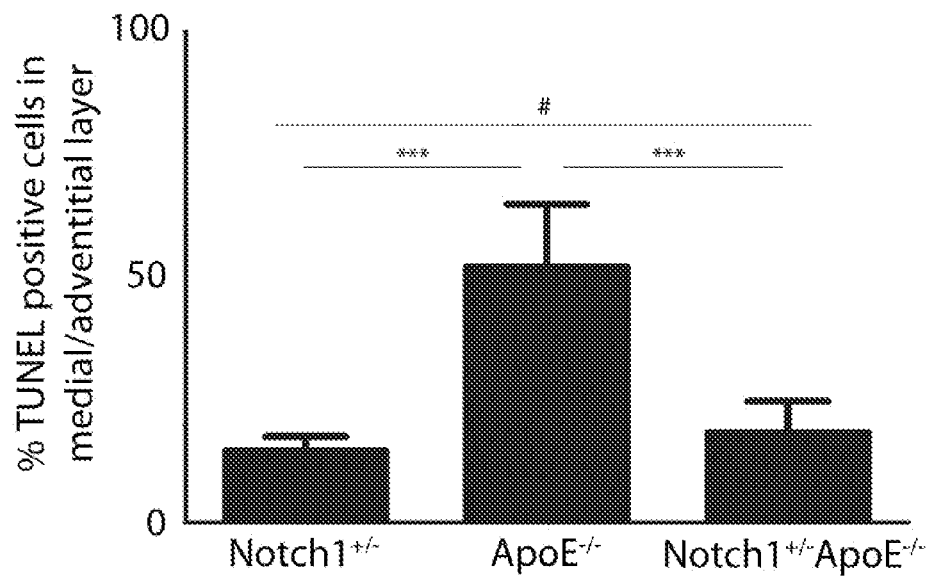

As expected, ApoE$^{-/-}$ mice treated with AngII demonstrated the cellular and architectural changes of typical AAA including thrombus formation, adventitial remodeling, presence of inflammatory cells and visible elastin degradation. The aorta of Notch1$^{+/-}$ApoE$^{-/-}$ mice infused with AngII displayed a well-defined lumen, with no visible elastin degradation and an almost complete absence of inflammatory cells. Minimal adventitial thickening was observed in the Notch1$^{+/-}$ and Notch1$^{+/-}$ApoE$^{-/-}$ mice. Histological examination of Notch1$^{+/-}$ mice treated with AngII or saline-treated controls also did not show any evidence of AAA. Decreased apoptosis was found in the aortic wall of Notch1$^{+/-}$ApoE$^{-/-}$ mice as compared to ApoE$^{-/-}$ mice treated with AngII. Quantitation of the TUNEL staining revealed that Notch1$^{+/-}$ApoE$^{-/-}$ mice demonstrated decreased number of apoptotic nuclei in endothelial (p value<0.01) as well as medial and adventitial layers (p value<0.001) of the aorta in response to AngII as compared to ApoE$^{-/-}$ mice (FIGS. 3 A and B). Of note, Notch1$^{+/-}$ApoE$^{-/-}$ mice demonstrated a modest increase in the apoptotic cell death in the endothelial layer but not in the medial and adventitial layers of the aortic wall with AngII treatment as compared to Notch1$^{+/-}$ mice as detected by TUNEL staining.

These data demonstrate that Notch1 haploinsufficiency significantly decreased the occurrence of pathological sequelae that are associated with AAA in an established mouse model.

Example 3

Notch1 Haploinsufficiency Reduces Macrophage Infiltration at Site of AAA

The influx of inflammatory cells, consisting of macrophages and lymphocytes, to the site of aneurysm formation is critical for the development of AAA [Daugherty et al., *Curr. Atheroscler. Rep.*, 4:222-227 (2002); Tieu et al., *J. Clin. Invest.*, 119:3637-3651 (2009); Golledge et al., *Circulation*, 118:2382-2392 (2008)]. Since monocyte recruitment and macrophage infiltration manifest at the early stages of AAA formation, the abdominal aorta was examined at day 7 and 28 of AngII infusion for the expression of the monocyte and macrophage marker (MOMA-2). Similar to AngII treatment for 28 days, the aorta of ApoE$^{-/-}$ mice infused with AngII for 7 days showed visible signs of luminal expansion and elastin degradation accompanied by apoptotic cell death along with increased expression of NICD which was absent in Notch1$^{+/-}$ApoE$^{-/-}$ mice. At both day 7 and day 28 of Ang II infusion, there was decreased expression of MOMA-2 in the abdominal aorta of Notch1$^{+/-}$ApoE$^{-/-}$ mice as compared to ApoE$^{-/-}$ mice. MCP-1 plays critical role in the recruitment and infiltration of macrophages in response to injury.

Figure 4:
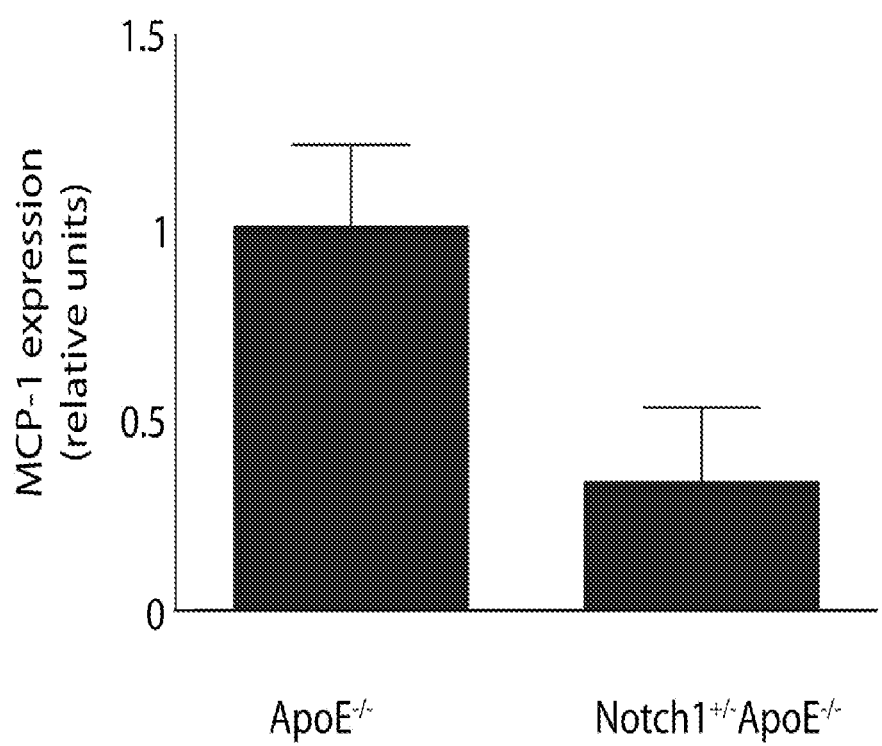
FIG. 4. Minimal macrophage recruitment and MCP-1 expression in the aorta of Notch1$^{+/-}$ApoE$^{-/-}$ mice after 7 and 28 days of AngII infusion. Double immunostaining with MOMA-2 and MCP-1 shows substantial macrophage infiltration in the adventitial layer at day 7 and day 28 in ApoE$^{-/-}$ mice in response to AngII. No double staining was seen in Notch1$^{+/-}$ApoE$^{-/-}$ mice at both timepoints. Merged panels demonstrate that MCP-1 expression is highly localized with the macrophage content in the adventitia of the aneurysmal aorta of ApoE$^{-/-}$ mice. No evidence of AAA is found in Notch1$^{+/-}$ApoE$^{-/-}$ mice after 7 days of AngII infusion as compared to ApoE$^{-/-}$ mice. Histologic section demonstrated disruption of the aortic wall and infiltration of inflammatory cells in the aorta of ApoE$^{-/-}$ mice by day 7 which was not seen in Notch1$^{+/-}$ApoE$^{-/-}$ mice. Degradation of the elastic lamina in ApoE$^{-/-}$ mice was observed as compared to normal elastic lamina in Notch1$^{+/-}$ApoE$^{-/-}$ mice.

Next, the expression of MCP-1 was examined in the abdominal aorta. Immunofluorescence and immunohistochemistry of the aneurysmal region revealed an increased expression of MCP-1 in the inflammatory cells in ApoE$^{-/-}$ mice, which was abrogated in the aorta of Notch1$^{+/-}$ApoE$^{-/-}$ mice at both 7 and 28 days of AngII treatment (FIG. 4). Double immunostaining (DIS) with MOMA-2 and MCP-1 suggested that many of the DAPI positive cells in the adventitial layer of ApoE$^{-/-}$ mice were immunopositive for MOMA-2 and MCP-1. DIS further revealed that increased MCP-1 was localized to regions of macrophage infiltration where visible elastin degradation was noted in AngII-treated ApoE$^{-/-}$ mice. Remarkably, there was a negligible co-expression of MCP-1 and MOMA-2 in Notch1$^{+/-}$ApoE$^{-/-}$ mice. Of note, red staining in the aortic medial layer corresponds to non-specific autofluorescence of elastin fibrils. Quantification of the MCP-1 immunostaining showed a significant decrease in the MCP-1 expression in the abdominal aorta of Notch1$^{+/-}$ApoE$^{-/-}$ mice as compared to ApoE$^{-/-}$ AngII (FIG. 4). Of note, the adventitial thickening observed in the abdominal aortic region of Notch1$^{+/-}$ApoE$^{-/-}$ mice was devoid of MCP-1 positive inflammatory cells. The data show that Notch1 haploinsufficiency results in the lack of macrophage recruitment and MCP-1 expression at the site of aneurysm formation in the AngII mouse model of AAA.

To further demonstrate the role of Notch1 signaling in macrophages to prevent AAA, bone marrow transplantation experiments were performed. ApoE$^{-/-}$ mice that received bone marrow-derived cells from Notch1$^{+/-}$;ApoE$^{-/-}$ mice did not develop AAA with AngII infusion, while Notch1$^{+/-}$;ApoE$^{-/-}$ mice that received bone marrow-derived cells from ApoE$^{-/-}$ mice without AngII infusion developed AAA. These studies demonstrated that haploinsufficiency of Notch1 specifically in bone marrow derived cells, which include macrophages, were responsible for the reduction in AAA development in the Ang-II induced mouse model.

Example 4

Inhibition of Notch1 Downregulates Expression of Inflammatory Mediators by Macrophages AngII is postulated to play a central role in initiating inflammation in the aorta by increasing the expression of chemokines (MCP-1), adhesion molecules (ICAM-1 and VCAM-1) and cytokines (IL-6, IL-1β, TNF-α) [Daugherty et al., Curr. Atheroscler. Rep., 4:222-227 (2002); Tieu et al., J. Clin. Invest., 119:3637-3651 (2009); Golledge et al., Circulation, 118:2382-2392 (2008); Guo et al., J. Interferon Cytokine Res., 31:351-361 (2011)]. To determine if Notch1 haploinsufficiency reduces the inflammatory response in the AngII model of AAA, the mRNA expression levels of a panel of cytokines, chemokines and pro-inflammatory mediators by real time quantitative RT-PCR (qRT-PCR) was examined in the aortas of ApoE$^{-/-}$ and Notch1$^{+/-}$ApoE$^{-/-}$ mice treated with AngII for 28 days.

The aorta was isolated from experimental mice at day 28 of AngII infusion and immediately frozen in RNA-later (Ambion, Austin, Tex.). Abdominal aorta of equal length was cut from the abdominal region of ApoE$^{-/-}$ and Notch1$^{+/-}$ApoE$^{-/-}$ mice and RNA was extracted using RNAqueous kit (Ambion, Austin, Tex.). RAW cells (264.7) were obtained from ATCC (Manassas, Va.) and were cultured following the manufacturer's instructions. Naïve macrophages were collected from the peritoneal cavity of ApoE$^{-/-}$ or Notch1$^{+/-}$ApoE$^{-/-}$ mice by standard protocol [Hans et al., Cardiovasc. Pathol., 185:1894-902 (2011); Hans et al., Cardiovasc. Res., 78:429-439 (2008); Oumouna-Benachour et al., Circulation, 115:2442-2450 (2007)]. The isolated macrophages were cultured in RPMI containing 10% FCS for 3 days and were then treated with 100 nM LPS or diluent for 3 h in RPMI containing 1% FCS. Following treatment, the macrophages were washed with cold PBS and RNA was extracted using RNAeasy kit (Qiagen, Valencia, Calif.). cDNA was synthesized using SuperScript® VILO™ cDNA Synthesis Kit (Invitrogen, Carlsbad, Calif.) and subjected to qRT-PCR by SYBR Green RT-PCR kit (Applied Biosystems, Foster City Calif.) using Applied Biosystems 7500 Fast Real-Time PCR System (Foster City Calif.). qRT-PCR was performed in triplicate and fold change determined by standardization to 18S rRNA. Results were normalized to the controls.

Figure 5A:
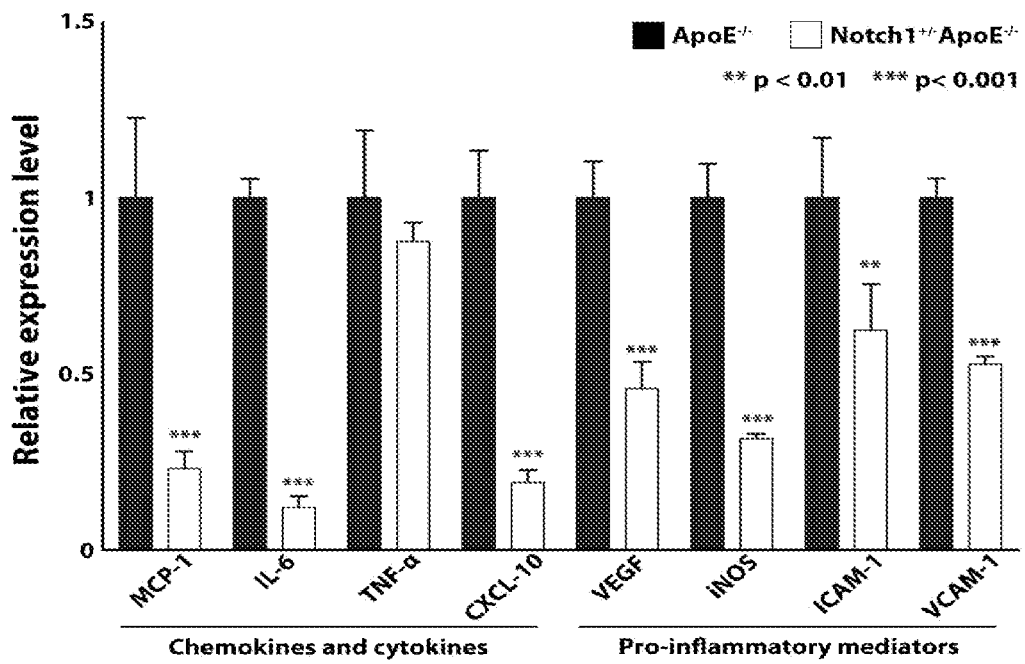
FIG. 5A-D. Inhibition of Notch1 downregulates expression of inflammatory mediators by macrophages. (A) qRT-PCR demonstrates reduced mRNA levels of MCP-1, IL-6, CXCL-10, VEGF, iNOS, ICAM-1 and VCAM-1 in the abdominal aorta of Notch1$^{+/-}$ApoE$^{-/-}$ mice as compared to ApoE$^{-/-}$ mice treated with AngII for 28 days (n=3, in triplicate). (B) Decreased expression of a similar panel of cytokines, chemokines and proinflammatory mediators as measured by qRT-PCR in (B) unstimulated or (C) LPS-stimulated (100 nM) RAW cells treated with 10 µM DAPT for 6 days as compared to untreated cells. (D) qRT-PCR demonstrates reduced expression of a similar panel of inflammatory mediators in LPS-stimulated primary macrophages isolated from the peritoneal cavity of Notch1$^{+/-}$ApoE$^{-/-}$ mice as compared ApoE$^{-/-}$ mice. *, p value<0.001; , p value<0.01; *p value<0.05; #, not significant.

Significant reduction of the expression of chemokines and cytokines (MCP-1, IL-6, CXCL-10) and the pro-inflammatory mediators (VEGF, iNOS, ICAM-1, VCAM-1) was found in the aorta of Notch1$^{+/-}$ApoE$^{-/-}$ mice as compared to ApoE$^{-/-}$ mice (FIG. 5A).

Figure 5B:
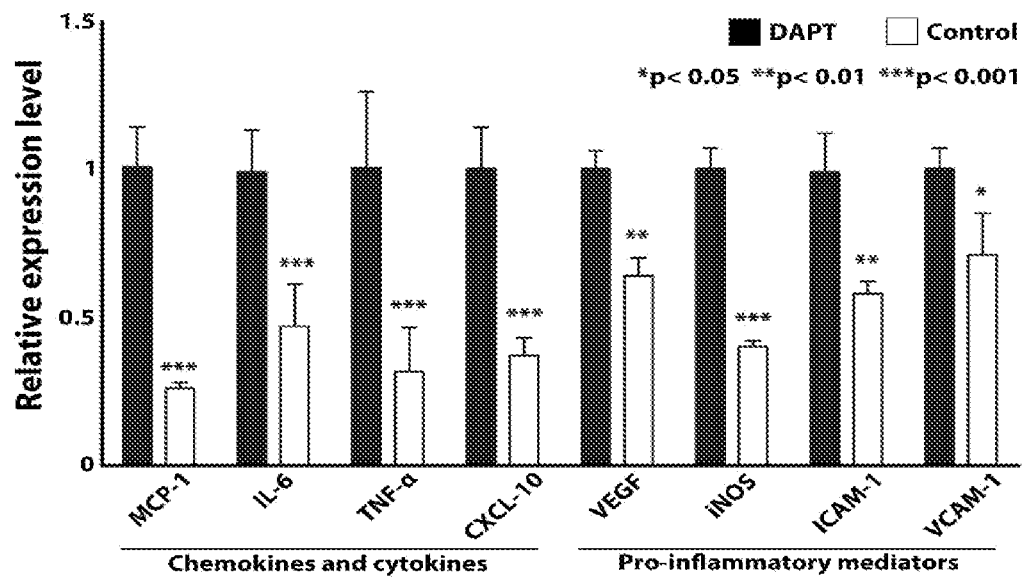
Figure 5C:
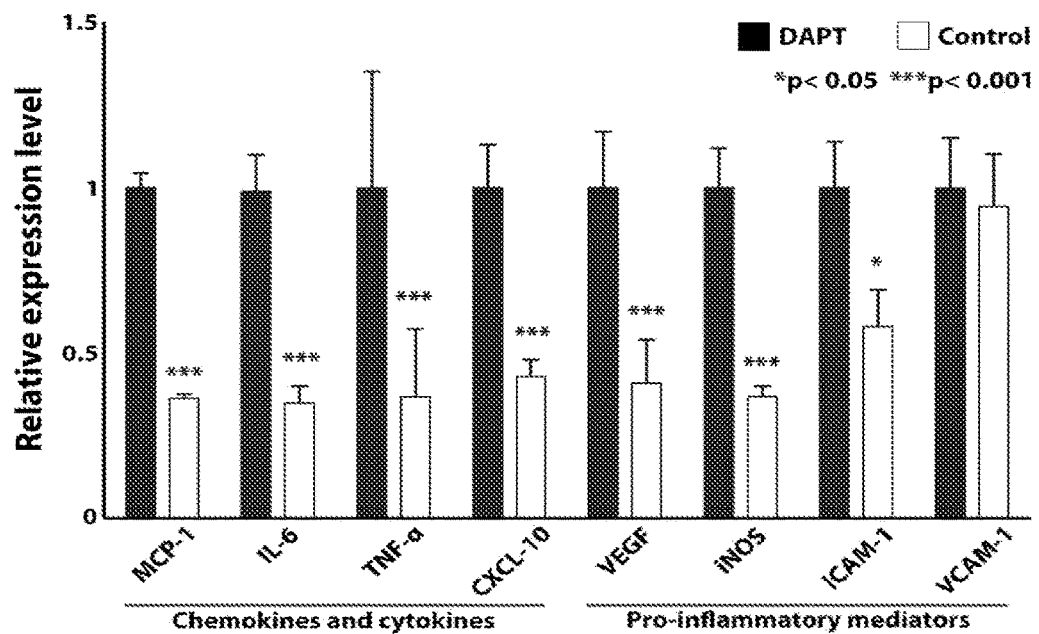
Figure 5D:
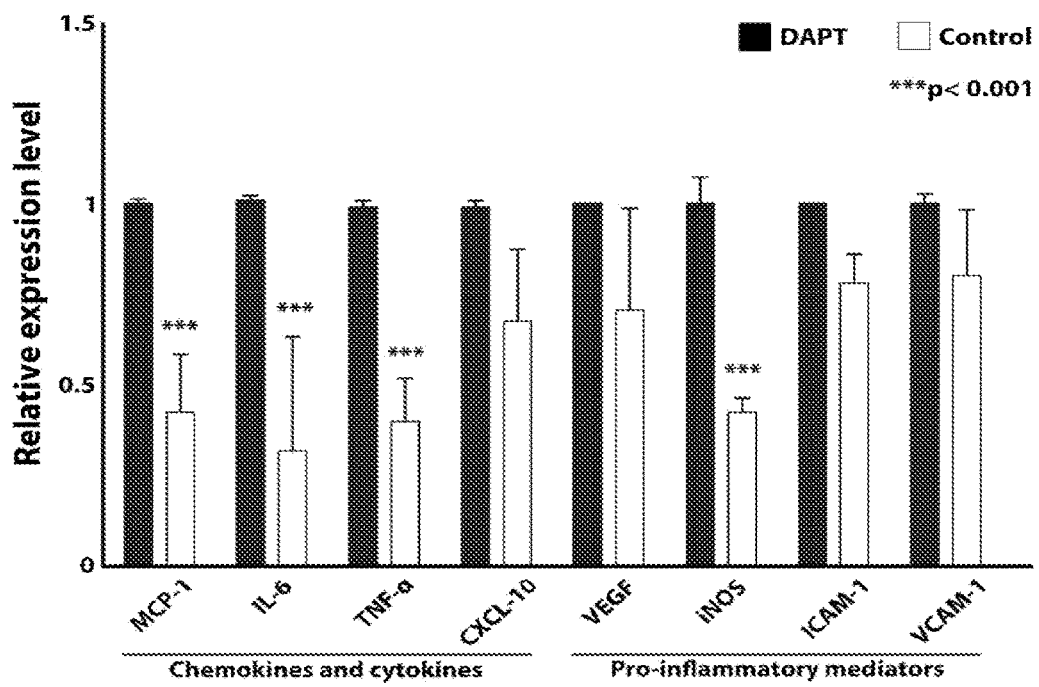

To further define the role of Notch1 in the inflammatory response, the effect of inhibition of Notch signaling on the production of inflammatory mediators in an immortal macrophage cell line (RAW 264.7) was studied. Chemical inhibition of Notch signaling with 10 μM DAPT (N—[N-(3,5-Difluorophenacetyl)-L-alanyl]-S-phenylglycine t-butyl ester) a γ-secretase inhibitor, for 6 days in RAW cells significantly decreased the expression of MCP-1, IL-6, TNF-α, CXCL-10, VEGF, iNOS, ICAM-1, and VCAM-1 as compared to untreated cells (FIG. 5B). To determine if similar changes in inflammatory gene expression occurred with an inflammatory stimulus, RAW cells were cultured and treated with 100 ng/ml lipopolysaccharide (LPS) for 3 hours. While expression of this panel of cytokines and inflammatory mediators was increased as compared to unstimulated cells (data not shown), pre-treatment with 10 μM DAPT resulted in significantly reduced expression of MCP-1, IL-6, TNF-α, CXCL-10, VEGF, iNOS, and ICAM-1 as compared to non-DAPT treated cells (FIG. 5C).

To determine if a similar decreased inflammatory response occurs in vivo, primary macrophages (PM) were isolated from the peritoneal cavity of ApoE$^{-/-}$ and Notch1$^{+/-}$ApoE$^{-/-}$ mice and subjected to LPS stimulation (100 ng/ml) for 3 hours. The mRNA expression levels for a panel of cytokines, chemokines and proinflammatory mediators were determined by qRT-PCR analysis using the primers shown below.

| Gene | Forward Primer | SEQ ID NO | Reverse Primer | SEQ ID NO |
|---|---|---|---|---|
| MCP-1 | 5'-CTG GAT CGG AAC CAA ATG AG-3' | 1 | 5'-AAG GCA TCA CAG TCC GAG TC-3' | 2 |
| IL-6 | 5'-CTA CCC CAA TTT CCA ATG CT-3' | 3 | 5'-ACC ACA GTG AGG AAT GTC CA-3' | 4 |

-continued

| Gene | Forward Primer | SEQ ID NO | Reverse Primer | SEQ ID NO |
|---|---|---|---|---|
| TNF-α | 5'-CCC ACT CTG ACC CCT TTA CT-3' | 5 | 5'-TTT GAG TCC TTG ATG GTC GT-3' | 6 |
| CXCL-10 | 5'-CCC ACG TGT TGA GAT CAT TG-3' | 7 | 5'-CAC TGG GTA AAG GGG AGT GA-3' | 8 |
| VEGF | 5'-GGC TGC TGT AAC GAT GAA GC-3' | 9 | 5'-TTA ACT CAA GCT GCC TCG C-3' | 10 |
| iNOS | 5'-CTC GGA GGT TCA CCT CAC TGT-3' | 11 | 5'-TCC TGA TCC AAG TGC TGC AGA-3' | 12 |
| ICAM-1 | 5'-GTG ATC CCT GGG CCT GGT G-3' | 13 | 5'-GGA AAC GAA TAC ACG GTG ATG G-3' | 14 |
| VCAM-1 | 5'-TAC CAG CTC CCA AAA TCC TG-3' | 15 | 5'-TCT GCT AAT TCC AGC CTC GT-3' | 16 |

The expression of MCP-1, IL-6, TNF-α and iNOS in the PM from Notch1$^{+/-}$ApoE$^{-/-}$ mice was ~60% less than in PM from ApoE$^{-/-}$ mice in response to LPS treatment. As expected, the expression of Notch1 was also reduced by about 60% in the macrophages from Notch1$^{+/-}$ mice.

In summary, Notch1 deficiency decreases the macrophage inflammatory response, as measured by cytokine and chemokine expression, at both basal levels and in response to external stress.

Example 5

Notch1 Haploinsufficiency Causes Defects in Macrophage Migration and Proliferation by Differentially Regulating M1/M2 Polarization The direct infiltration of active macrophages and lymphocytes was assessed by FACS analysis at the site lesion of the mice of Example 4.

The suprarenal abdominal aorta of Notch1$^{+/-}$; ApoE$^{-/-}$ mice contained a decreased number of inflammatory macrophages with Cd11b and Cd14 staining as compared to ApoE$^{-/-}$ mice after 7 days of AngII infusion. Notch1 haploinsufficiency did not alter the differentiation of Cd4$^+$ or Cd8$^+$ lymphocytes at the site of injury, although total number of Cd3$^+$ T lymphocytes was significantly decreased in the suprarenal aorta of Notch1$^{+/-}$;ApoE$^{-/-}$ mice as compared to ApoE$^{-/-}$ mice after 7 days of AngII infusion as determined by FACS analysis and immunostaining. Interestingly, no significant difference was observed in the absolute number of Cd3$^+$ T cells in the spleen or peripheral blood of these experimental mice.

Next, the effect of Notch 1 signaling on macrophage migration and proliferation was examined. In a classical scratch assay, Notch1 haploinsufficiency significantly decreased the migration of peritoneal-derived primary macrophages, towards the injury site after 24 h. After 24 h, decreased proliferation was observed in Notch1$^{+/-}$;ApoE$^{-/-}$ macrophages as compared to ApoE$^{-/-}$ macrophages as determined by staining with proliferation marker Ki67. Increased Ki67 staining localized with macrophages was also observed in the abdominal aorta of ApoE$^{-/-}$ mice, whereas no such co-expression was observed in the aorta of Notch1$^{+/-}$; ApoE$^{-/-}$ mice. In a transwell culture system, FMLP (a potent and specific chemotactic agent)-induced migration of primary macrophages was significantly reduced with Notch1 haploinsufficiency.

Then, to determine, if Notch1 haploinsufficiency affects proliferation of primary macrophages in vivo, thioglycollate injection was used to elicit recruitment of macrophages to the peritoneal cavity. Notch1 haploinsufficiency resulted in the diminished influx of macrophages by almost 50% at day 4 of the thioglycollate infusion. Recent studies have suggested integral role for Notch1 to regulate M1 polarization of naïve macrophages mediated by synthesis of interferon regulatory factor 8 (Irf8) protein. Expression of Irf8 was upregulated in the abdominal aorta of ApoE$^{-/-}$ mice in response to AngII at day 7 whereas Notch1 haploinsufficiency prevented upregulation of Irf8. To determine whether Notch1 regulates polarization of macrophages, markers for inflammatory M1-associated genes were examined in response to LPS/Ifn-γ stimulation and M2-associated genes in response to Il4 stimulation in the bone-marrow derived macrophages (BMDM). Increased expression of Il6, Il12, Tnf-α and iNOS genes was observed in the BMDM of ApoE$^{-/-}$ mice in response to LPS/Ifn-γ whereas no change was seen from with Notch1 haploinsufficiency. More importantly, in response to Il4, the expression of arginase1 (Arg1) and macrophage galactose N-acetyl-galactosamine specific lectin 2 (Mgl$_2$) was higher in BMDM from Notch1$^{+/-}$; ApoE$^{-/-}$ mice as compared to ApoE$^{-/-}$ mice suggesting that Notch1 deficient macrophages are polarized towards the M2 fate. The M1 polarization of macrophages in response to LPS/Ifn-γ was further confirmed by FACS analysis. M1 polarization of macrophages in ApoE$^{-/-}$ mice was associated with increased Irf8 staining, which was reduced by Notch1 haploinsufficiency.

Taken together, the results demonstrate that Notch1 haploinsufficiency causes defects in the migration and proliferation functions of macrophages by differentially regulating M1/M2 polarization of macrophages thus preventing them from infiltrating the site of aneurysm formation in the AngII mouse model.

Example 6

Prophylactic Pharmacological Inhibition of Notch Signaling Attenuates Aneurysm Development in an AngII-Induced Mouse Model of AAA While the data demonstrate a role for Notch signaling in macrophages, Notch1 is known to be necessary for the proper development of the aorta [Gridley, Development, 134:2709-2718 (2007)]. To determine if protective effects of Notch1 haploinsufficiency on AAA formation are specific to reduced Notch1 signaling and to investigate therapeutic potential of Notch1 inhibition, whether pharmacological inhibition of Notch protects against the formation of AAA was tested in ApoE$^{-/-}$ mice infused with AngII.

Figures 2A, 2B:
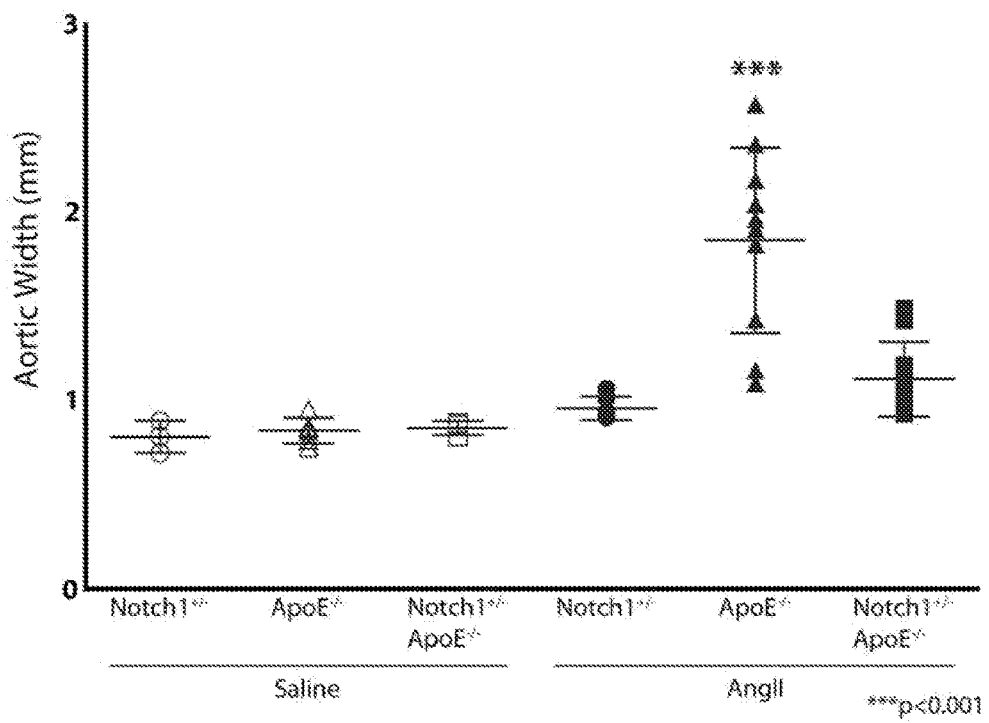
FIG. 2. Quantitative measurement of aortic width (mm) of all experimental mice. Mean and standard deviations are shown. Each individual animal is represented by a symbol. ***, p value<0.001 when comparing ApoE$^{-/-}$ with AngII versus ApoE$^{-/-}$ with saline or Notch1$^{+/-}$ApoE$^{-/-}$ treated with AngII. Table 1 shows the incidence of AAA in Notch1$^{+/-}$, ApoE$^{-/-}$ and Notch1$^{+/-}$ApoE$^{-/-}$ mice treated with saline or AngII. AngII infusion did not result in abdominal aortic aneurysm in wild type mice. Histologic section of the abdominal aorta in these wild type mice shows the absence of the characteristic markers of AAA. p value<0.05 when comparing ApoE$^{-/-}$ with AngII versus Notch1$^{+/-}$ApoE$^{-/-}$ treated with AngII. Scale bar represents 1 mm.
Figures 6A, 6B, 6C:
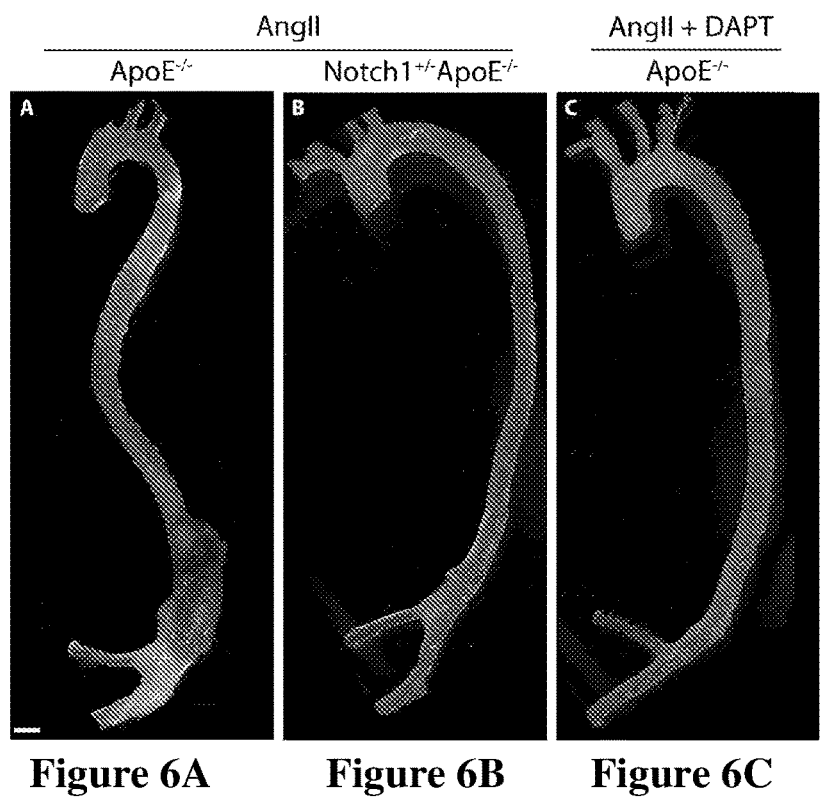
FIG. 6A-D. Prophylactic pharmacological inhibition of Notch signaling prior attenuates aneurysm development in an AngII-induced mouse model of AAA. (A-C) Representative aortas from ApoE$^{-/-}$ (A), Notch1$^{+/-}$ApoE$^{-/-}$ (B), and ApoE$^{-/-}$ mice treated with 10 mg/kg of DAPT (C). All mice received AngII infusion, scale bar represents 1 mm. Histologic sections show no evidence of abdominal aneurysm in ApoE$^{-/-}$ that received DAPT similar to Notch1$^{+/-}$ApoE$^{-/-}$ mice. Scale bar represents 50 microns. (D) Quantitative measurement of aortic width (mm) in these mice. Means and standard deviations are shown and each symbol represents an individual animal. **p value<0.01 when comparing ApoE$^{-/-}$ mice to ApoE$^{-/-}$ mice treated with DAPT.
Figure 6D:
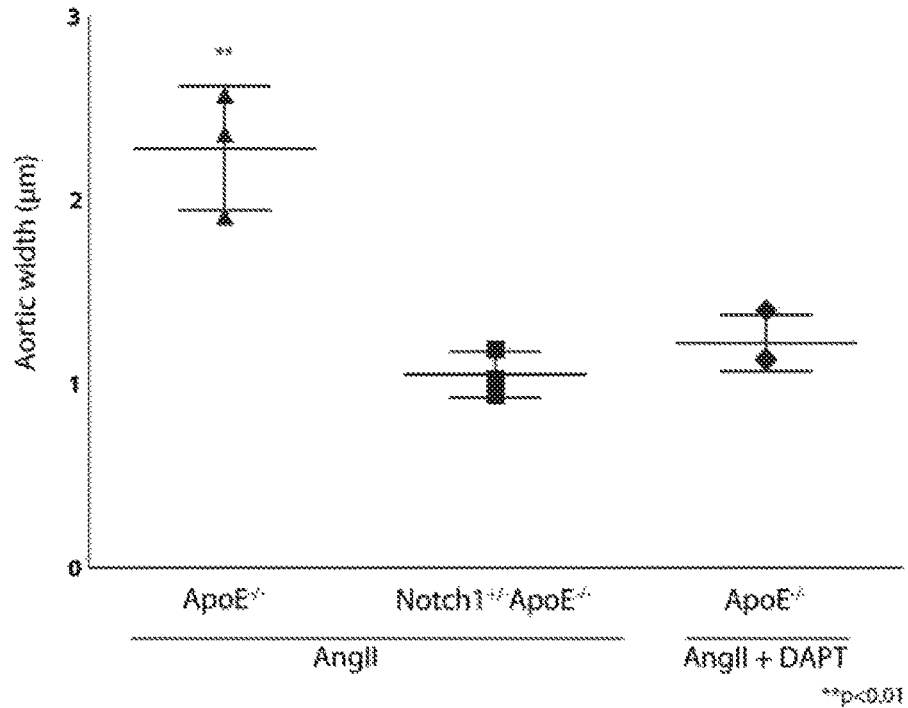

Mice were treated with DAPT (10 mg/kg) three times a week, starting one week prior to initiating the AngII infusion and continuing for 28 days. Treatment with DAPT resulted in a statistically significant reduction in the aortic diameter and incidence of AAA as compared to untreated ApoE$^{-/-}$ mice and was similar to Notch1$^{+/-}$ApoE$^{-/-}$ mice (FIG. 6). Histologic analysis of the aorta of the ApoE$^{-/-}$ mice treated with DAPT demonstrated normal aortic wall architecture without infiltration of inflammatory cells as compared to untreated mice. Of note, this experiment was performed concurrently with a subset of experiments shown in FIG. 2 and only ApoE$^{-/-}$ and Notch1$^{+/-}$ApoE$^{-/-}$ mice performed simultaneously are shown for comparison. These studies demonstrate that the reduced incidence of AAA seen with genetic deficiency of Notch1 are not the result of differences in the aortic wall and also demonstrate a potential therapeutic strategy for treatment of AAA.

The clinical management of AAA is based on the control of primary risk factors such as tobacco use, dyslipidemia, hypertension, atherosclerosis and infection. At present, there are no drugs that specifically target AAA. To prevent the progression or stimulate the regression of established AAA, there is a critical need to develop pharmacologic interventions that can selectively target one or more features of AAA [Baxter et al., *Circulation*, 117:1883-1889 (2008); Hurks et al., *European Journal of Vascular and Endovascular Surgery*, 39:569-576 (2010); Cooper et al., *Postgraduate Medical Journal*, 85:688-692 (2009)]. A number of strategies have been proposed to achieve the objective of impeding AAA progression, but available options fall short of this goal. The results presented herein demonstrate that Notch1 is an important player in the inflammatory process in the setting of AAA and indicate treatment with Notch inhibitors for slowing aneurysm development and preventing aortic dissection/rupture, particularly for those individuals who have not yet reached the threshold diameter for surgical intervention.

Example 7

Therapeutic Pharmacological Inhibition of Notch Signaling Attenuates Aneurysm Development in an AngII-Induced Mouse Model of AAA The data above show that Notch1 inhibition prevents the initiation of AAA in ApoE$^{-/-}$ mice. Next, whether Notch1 inhibition would inhibit progression of AAA after the onset of inflammation was tested, since from the clinical standpoint pharmacological treatment of AAA could be initiated in aortas with established disease.

In the study, mice were divided into four groups:
ApoE$^{-/-}$ mice with AngII plus vehicle for 28 days (n=6);
ApoE$^{-/-}$ mice with AngII plus DAPT (7 days prior to AngII infusion, n=6);
ApoE$^{-/-}$ mice with AngII plus DAPT (3 days after AngII infusion, n=9); and
ApoE$^{-/-}$ mice with AngII plus DAPT (8 days after AngII infusion, n=9).

These time periods were carefully selected to determine the effect of Notch inhibition on the formation of AAA before the onset of disease (-7 days), at day 3 (onset of inflammation) and day 8 (elastin degradation and cellular remodeling).

NOTCH inhibitor (DAPT; 10 mg/kg; three time a day in corn oil) given at day 3 and day 8 after the AngII infusion reduced the progression of active AAA in the mouse model. The two time intervals were selected since the data herein and the studies done by Alan Daugherty's group and others have shown that the earliest changes in response to AngII are noted as early as 48 hours [Daugherty et al., *Curr. Atheroscler. Rep.*, 4:222-227 (2002); Daugherty et al., *Arterioscler. Thromb. Vasc. Biol.*, 24:429-434 (2004)]. During this interval, there was medial accumulation of macrophages that occupied discrete areas in the region that later develops into aneurysms. Macrophage migration into the aortic media associated with elastin disintegration after 48 hours of Ang II infusion to ApoE$^{-/-}$ mice. Medial destruction leading to localized dissection and accumulation of intramural hematoma is found after 7 days of AngII infusion into these mice.

Notch inhibition significantly decreased the maximal abdominal aortic width at day 28 in response to DAPT treatment at day 3 and day 8 suggesting that Notch inhibitor impedes the progression of pre-established/active aneurysmal disease or may actually regress it. See, FIG. 7.

Figure 8:
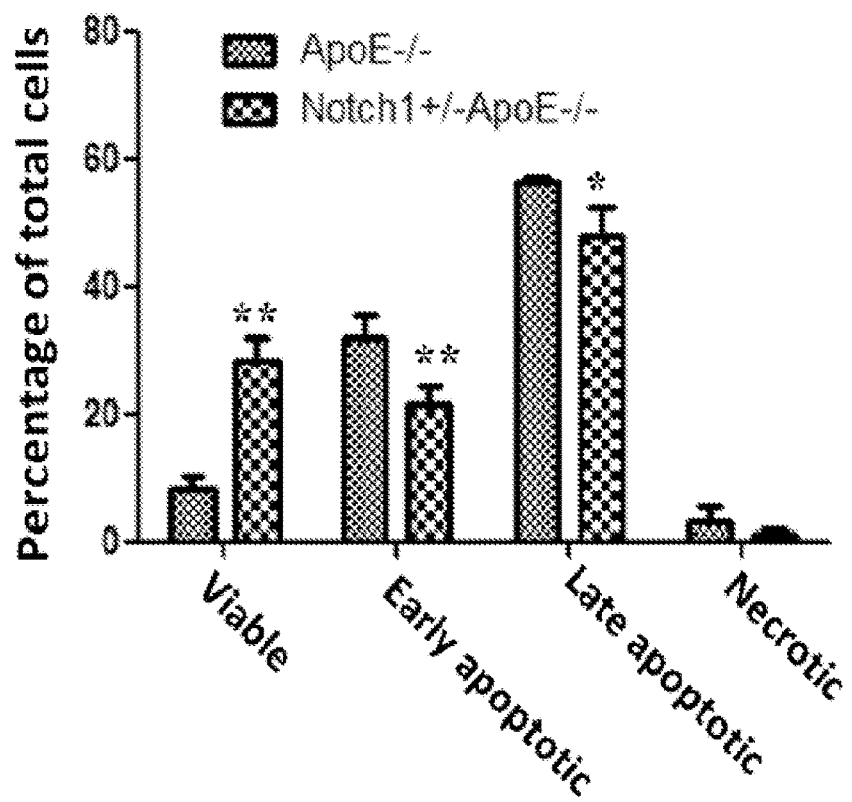
FIG. 8. Notch1 deficiency decreases apoptotic cell death of aortic smooth muscle cells.

Primary smooth muscle cells were isolated from ApoE$^{-/-}$ and Notch1$^{+/-}$;ApoE$^{-/-}$ mice to further characterize the role of Notch1 deficiency on apoptotic cell death. Notch1 deficiency protected against apoptotic cell death of smooth muscle cells in response to LPS treatment as determined by flow cytometry. See, FIG. 8.

Overall, the data suggests that Notch1 inhibition may protect against the abdominal aneurysmal disease by multifactorial mechanisms.

Example 8

Pharmacological Inhibition of Notch Signaling Prevents the Progression of Active AAA in an AngII-Induced Mouse Model Active aneurysm was introduced in ApoE$^{-/-}$ mice (n=36) by administering AngII. DAPT (10 mg/kg; 3 times a week) was injected in these mice starting either 3 days (Group II; n=12) or 8 days (Group III; n=12) after AngII infusion. Group I (n=12) received vehicle (10% alcohol in corn oil) only. The time periods were chosen so that a small aortic dilation is established before DAPT is administered.

Figure 9A:
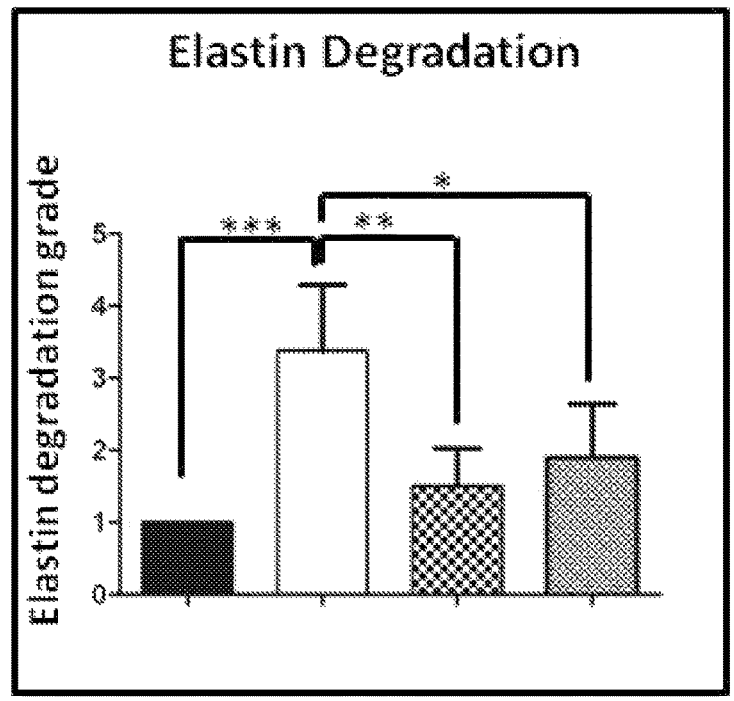
FIG. 9. Pharmacologic inhibition of Notch signaling stabilizes the progression of AAA by preventing ECM degradation and synthesis of tropoelastin.
Figure 9B:
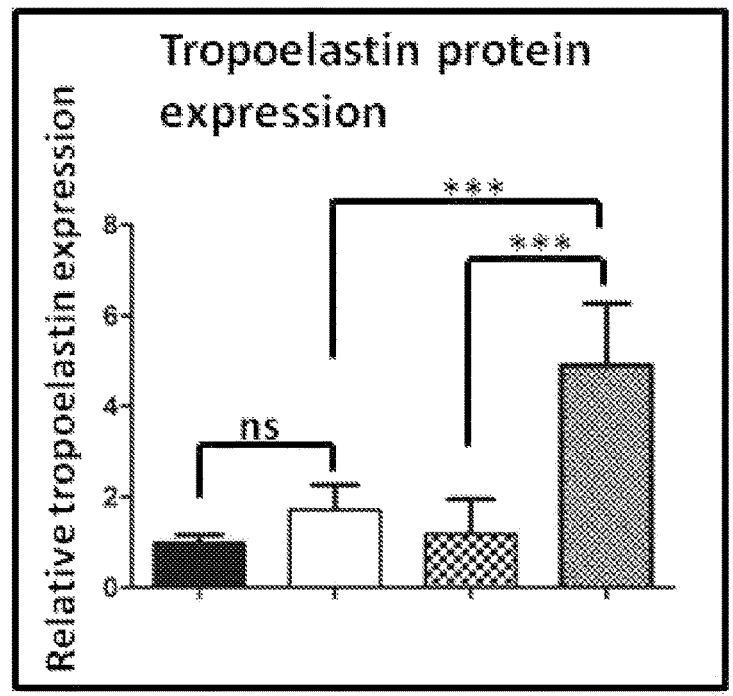
Figure 9C:
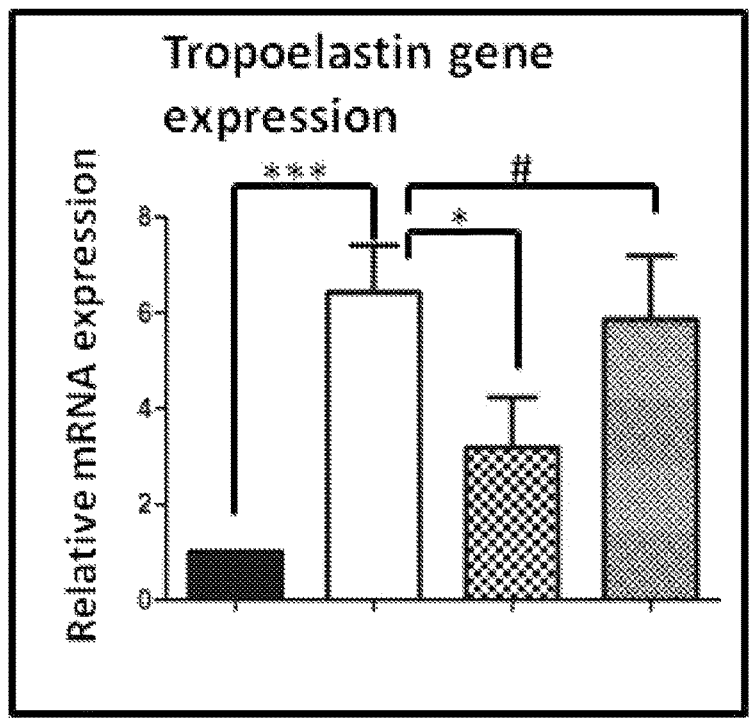
Figure 9D:
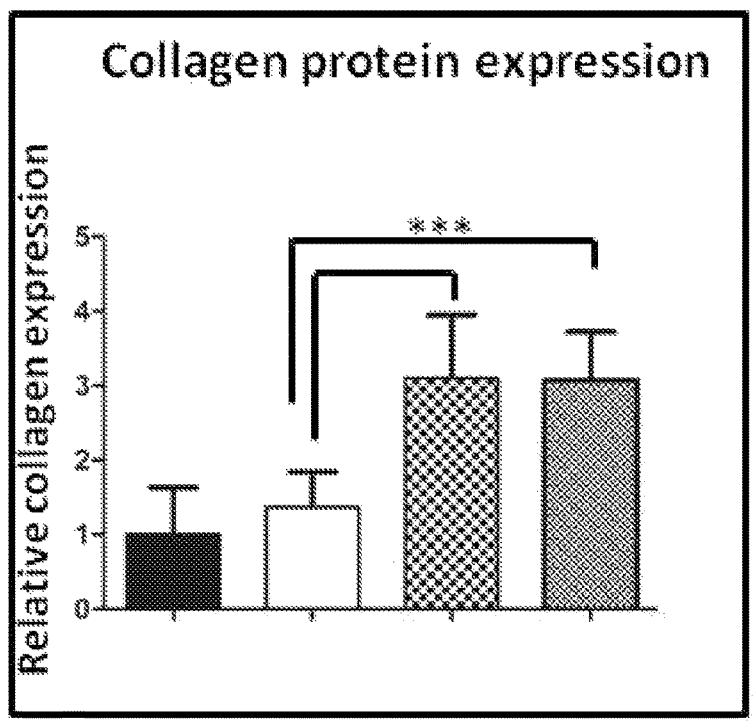

DAPT treatment significantly reduced luminal expansion of the abdominal aorta in both the groups as compared to vehicle-treated ApoE$^{-/-}$ mice (p<0.05) as detected by echocardiography. DAPT treatment also prevented characteristic aneurysmal traits of elastin fragmentation (FIG. 9A) and aortic remodeling in both the groups as detected by histology. Marginal increase in macrophage content (CD-68) was observed in Group III compared to Group II, but was significantly less than Group I. However, the increased macrophage content in Group III was not associated with increased monocyte chemotactic protein-1 suggesting that DAPT treatment prevents continuous influx of macrophages. In vitro data suggest that Notch1 inhibition decreases M1 polarization of macrophages and promotes their M2 fate. Interestingly, increased expression of newly synthesized tropoelastin (FIGS. 9B and 9C) and collagen (FIG. 9D) staining was detected in Group III suggesting that Notch1 inhibition triggered repair of the vascular injury in the absence of recruitment of inflammatory macrophages. The increased collagen content in the aorta of ApoE$^{-/-}$ mice in response to AngII provides stability to the tissue against sudden rupture. Expression of MMP2 and MMP9 was also decreased in the aortas of Group II and Group III compared to Group I (vehicle) as determined by quantitative real-time PCR and immunohistochemistry.

These results demonstrate that Notch inhibition stabilizes the progression of AAA and is associated with increased elastin and collagen regeneration as well as decreased MMP activity. The use of Notch inhibitors is indicated for the treatment of AAA.

While the present invention has been described in terms of specific embodiments, it is understood that variations and modifications will occur to those skilled in the art. Accordingly, only such limitations as appear in the claims should be placed on the invention.

All documents referred to throughout this application are hereby incorporated by reference in their entirety.

We claim:

1. A method of treating a patient developing or suffering from an aortic abdominal aneurysm (AAA) comprising administering a therapeutically effective amount of an inhibitor of Notch1 signaling to the patient,
    whereby Notch1 signaling is inhibited in macrophages slowing or halting the progression of the AAA.

2. The method of claim 1 wherein the inhibitor is a specific inhibitor of Notch1 signaling.

3. The method of claim 1 or 2 wherein the inhibitor is a γ-secretase inhibitor.

4. The method of claim 3 wherein the inhibitor is N—[N-(3,5-Difluorophenacetyl)-L-alanyl]-S-phenylglycine t-butyl ester (DAPT).

5. The method of claim 3 wherein the inhibitor is cis-3-[3-[(3-chlorophenyl)sulfonyl]-4-(2,5-difluorophenyl)cyclohexyl]propanoicacid.

6. The method of claim 1 wherein the inhibitor stimulates the regression of the AAA.

* * * * *